(12) United States Patent
Roschak

(10) Patent No.: US 8,784,400 B2
(45) Date of Patent: *Jul. 22, 2014

(54) DEVICES FOR DELIVERING SUBSTANCES THROUGH AN EXTRA-ANATOMIC OPENING CREATED IN AN AIRWAY

(75) Inventor: Edmund J. Roschak, Mission Viejo, CA (US)

(73) Assignee: Broncus Medical Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/473,355

(22) Filed: May 16, 2012

(65) Prior Publication Data

US 2012/0232523 A1    Sep. 13, 2012

Related U.S. Application Data

(63) Continuation of application No. 12/939,968, filed on Nov. 4, 2010, now Pat. No. 8,608,724, which is a continuation of application No. 11/538,950, filed on Oct. 5, 2006, now Pat. No. 8,409,167, which is a continuation-in-part of application No. 10/895,022, filed on Jul. 19, 2004, now abandoned.

(51) Int. Cl.
*A61M 31/00* (2006.01)

(52) U.S. Cl.
USPC .................................... 604/506; 604/500

(58) Field of Classification Search
USPC .................. 604/500, 506, 507, 508, 510
See application file for complete search history.

(56) References Cited

U.S. PATENT DOCUMENTS

| | | | |
|---|---|---|---|
| 2,127,903 | A | 8/1938 | Bowen |
| 3,174,851 | A | 3/1965 | Buehler et al. |
| 3,351,463 | A | 11/1967 | Rozner et al. |
| 3,406,685 | A | 10/1968 | May |
| 3,433,226 | A | 3/1969 | Boyd |
| 3,556,079 | A | 1/1971 | Omizo |
| 3,565,062 | A | 2/1971 | Kuris |
| 3,617,060 | A | 11/1971 | Lezzi |
| 3,707,151 | A | 12/1972 | Jackson |
| 3,753,700 | A | 8/1973 | Harrison et al. |
| 3,779,234 | A | 12/1973 | Eggleton et al. |
| 3,823,717 | A | 7/1974 | Pohlman et al. |
| 3,874,388 | A | 4/1975 | King et al. |
| 3,889,688 | A | 6/1975 | Eamkaow |
| 3,942,530 | A | 3/1976 | Northeved |
| 4,249,539 | A | 2/1981 | Vilkomerson et al. |

(Continued)

FOREIGN PATENT DOCUMENTS

| | | |
|---|---|---|
| EP | 0347098 A2 | 12/1989 |
| EP | 0443256 A1 | 8/1991 |

(Continued)

OTHER PUBLICATIONS

Choong, C., et al., "Feasibility and safety of airway bypass stent placement and influence of topical mitomycin C on stent patency," *J. Thorac. Cardiovasc Surg.*, 129:632-638, 2005.

(Continued)

*Primary Examiner* — Bhisma Mehta
(74) *Attorney, Agent, or Firm* — Levine Bagade Han LLP

(57) ABSTRACT

Devices and methods for delivering substances to lung tissue through an extra-anatomic passage created in an airway.

20 Claims, 19 Drawing Sheets

(56) References Cited

U.S. PATENT DOCUMENTS

| | | |
|---|---|---|
| 4,249,541 A | 2/1981 | Pratt |
| 4,319,580 A | 3/1982 | Colley et al. |
| 4,324,235 A | 4/1982 | Beran |
| 4,327,739 A | 5/1982 | Chmiel et al. |
| 4,332,254 A | 6/1982 | Lundquist |
| 4,355,426 A | 10/1982 | MacGregor |
| 4,407,294 A | 10/1983 | Vilkomerson |
| 4,431,006 A | 2/1984 | Trimmer et al. |
| 4,469,142 A | 9/1984 | Harwood |
| 4,503,569 A | 3/1985 | Dotter |
| 4,534,761 A | 8/1985 | Raible |
| 4,538,606 A | 9/1985 | Whited |
| 4,538,618 A | 9/1985 | Rosenberg et al. |
| 4,582,067 A | 4/1986 | Silverstein et al. |
| 4,583,969 A | 4/1986 | Mortensen |
| 4,622,968 A | 11/1986 | Persson |
| 4,655,771 A | 4/1987 | Wallsten |
| 4,658,817 A | 4/1987 | Hardy |
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,702,252 A | 10/1987 | Brooks et al. |
| 4,706,689 A | 11/1987 | Man |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,767,627 A | 8/1988 | Caldwell et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,781,676 A | 11/1988 | Schweighardt et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,855,563 A | 8/1989 | Beresnev et al. |
| 4,869,268 A | 9/1989 | Yoon |
| 4,870,953 A | 10/1989 | Don Micheal et al. |
| 4,887,606 A | 12/1989 | Yock et al. |
| 4,892,098 A | 1/1990 | Sauer |
| 4,892,099 A | 1/1990 | Ohkawa et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,921,483 A | 5/1990 | Wijay et al. |
| 4,924,863 A | 5/1990 | Sterzer |
| 4,930,525 A | 6/1990 | Palestrant |
| 4,936,281 A | 6/1990 | Stasz |
| 4,955,377 A | 9/1990 | Lennox et al. |
| 4,957,508 A | 9/1990 | Kaneko et al. |
| 4,966,162 A | 10/1990 | Wang |
| 4,967,753 A | 11/1990 | Haase et al. |
| 4,973,301 A | 11/1990 | Nissenkorn |
| 4,976,690 A | 12/1990 | Solar et al. |
| 4,977,898 A | 12/1990 | Schwarzschild et al. |
| 4,991,602 A | 2/1991 | Amplatz et al. |
| 5,002,058 A | 3/1991 | Martinelli |
| 5,030,201 A | 7/1991 | Palestrant |
| 5,042,981 A | 8/1991 | Gross |
| 5,047,026 A | 9/1991 | Rydell |
| 5,054,483 A | 10/1991 | Marten et al. |
| 5,061,275 A | 10/1991 | Wallsten et al. |
| 5,064,435 A | 11/1991 | Porter |
| 5,069,664 A | 12/1991 | Guess et al. |
| 5,081,993 A | 1/1992 | Kitney et al. |
| 5,100,423 A | 3/1992 | Fearnot |
| 5,102,417 A | 4/1992 | Palmaz |
| 5,105,816 A | 4/1992 | Shimura et al. |
| 5,105,817 A | 4/1992 | Uchibori et al. |
| 5,123,917 A | 6/1992 | Lee |
| 5,125,926 A | 6/1992 | Rudko et al. |
| 5,127,917 A | 7/1992 | Niederhauser et al. |
| 5,131,394 A | 7/1992 | Gehlbach |
| 5,145,684 A | 9/1992 | Liversidge et al. |
| 5,148,809 A | 9/1992 | Biegeleisen-Knight et al. |
| 5,155,435 A | 10/1992 | Kaufman et al. |
| 5,170,793 A | 12/1992 | Takano et al. |
| 5,178,635 A | 1/1993 | Gwon et al. |
| 5,190,528 A | 3/1993 | Fonger et al. |
| 5,201,316 A | 4/1993 | Pomeranz et al. |
| 5,209,721 A | 5/1993 | Wilk |
| 5,220,924 A | 6/1993 | Frazin |
| 5,226,421 A | 7/1993 | Frisbie et al. |
| 5,234,447 A | 8/1993 | Kaster et al. |
| 5,238,027 A | 8/1993 | Lee |
| 5,246,011 A | 9/1993 | Caillouette |
| 5,246,014 A | 9/1993 | Williams et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,263,992 A | 11/1993 | Guire |
| 5,269,326 A | 12/1993 | Verrier |
| 5,273,529 A | 12/1993 | Idowu |
| 5,275,166 A | 1/1994 | Vaitekunas et al. |
| 5,282,799 A | 2/1994 | Rydell |
| 5,282,824 A | 2/1994 | Gianturco |
| 5,287,861 A | 2/1994 | Wilk |
| 5,295,484 A | 3/1994 | Marcus et al. |
| 5,299,578 A | 4/1994 | Rotteveel et al. |
| 5,304,200 A | 4/1994 | Spaulding |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,318,564 A | 6/1994 | Eggers |
| 5,320,106 A | 6/1994 | Tanaka |
| 5,330,500 A | 7/1994 | Song |
| 5,334,146 A | 8/1994 | Ozasa |
| 5,334,183 A | 8/1994 | Wuchinich |
| 5,334,210 A | 8/1994 | Gianturco |
| 5,338,305 A | 8/1994 | Plyley et al. |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |
| 5,366,504 A | 11/1994 | Andersen et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,413,601 A | 5/1995 | Keshelava |
| 5,421,955 A | 6/1995 | Lau |
| 5,425,739 A | 6/1995 | Jessen |
| 5,427,107 A | 6/1995 | Milo et al. |
| 5,429,144 A | 7/1995 | Wilk |
| 5,435,314 A | 7/1995 | Dias |
| 5,441,515 A | 8/1995 | Khosravi et al. |
| 5,443,498 A | 8/1995 | Fontaine |
| 5,443,843 A | 8/1995 | Curatolo et al. |
| 5,452,733 A | 9/1995 | Sterman et al. |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |

(56) References Cited

U.S. PATENT DOCUMENTS

| | | |
|---|---|---|
| 5,470,308 A | 11/1995 | Edwards et al. |
| 5,474,075 A | 12/1995 | Goldberg et al. |
| 5,474,543 A | 12/1995 | McKay |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,509,900 A | 4/1996 | Kirkman |
| 5,514,154 A | 5/1996 | Lau et al. |
| 5,520,684 A | 5/1996 | Imran |
| 5,522,822 A | 6/1996 | Phelps et al. |
| 5,524,630 A | 6/1996 | Crowley |
| 5,527,292 A | 6/1996 | Adams et al. |
| 5,527,324 A | 6/1996 | Krantz et al. |
| 5,531,780 A | 7/1996 | Vachon |
| 5,536,240 A | 7/1996 | Edwards et al. |
| 5,540,713 A | 7/1996 | Schnepp-Pesch et al. |
| 5,545,195 A | 8/1996 | Lennox et al. |
| 5,545,208 A | 8/1996 | Wolf et al. |
| 5,545,210 A | 8/1996 | Hess et al. |
| 5,554,118 A | 9/1996 | Jang |
| 5,554,152 A | 9/1996 | Aita et al. |
| 5,554,181 A | 9/1996 | Das |
| 5,555,886 A | 9/1996 | Weng et al. |
| 5,562,922 A | 10/1996 | Lambert |
| 5,564,434 A | 10/1996 | Halperin et al. |
| 5,571,086 A | 11/1996 | Kaplan et al. |
| 5,571,180 A | 11/1996 | Blom |
| 5,573,531 A | 11/1996 | Gregory |
| 5,575,815 A | 11/1996 | Slepian et al. |
| 5,575,818 A | 11/1996 | Pinchuk |
| 5,588,432 A | 12/1996 | Crowley |
| 5,593,417 A | 1/1997 | Rhodes |
| 5,593,442 A | 1/1997 | Klein |
| 5,596,989 A | 1/1997 | Morita |
| 5,607,444 A | 3/1997 | Lam |
| 5,615,679 A | 4/1997 | Ri et al. |
| 5,616,608 A | 4/1997 | Kinsella et al. |
| 5,618,301 A | 4/1997 | Hauenstein et al. |
| 5,629,678 A | 5/1997 | Gargano et al. |
| 5,629,687 A | 5/1997 | Sutton et al. |
| 5,630,837 A | 5/1997 | Crowley |
| D380,266 S | 6/1997 | Boatman et al. |
| 5,638,819 A | 6/1997 | Manwaring et al. |
| 5,645,559 A | 7/1997 | Hachtman et al. |
| 5,647,871 A | 7/1997 | Levine et al. |
| 5,653,746 A | 8/1997 | Schmitt |
| 5,655,548 A | 8/1997 | Nelson et al. |
| 5,658,279 A | 8/1997 | Nardella et al. |
| 5,658,280 A | 8/1997 | Issa |
| 5,672,172 A | 9/1997 | Zupkas |
| 5,674,242 A | 10/1997 | Phan et al. |
| 5,674,277 A | 10/1997 | Freitag |
| 5,674,298 A | 10/1997 | Levy et al. |
| 5,678,555 A | 10/1997 | O'Connell |
| 5,682,880 A | 11/1997 | Brain |
| 5,693,085 A | 12/1997 | Buirge et al. |
| 5,702,418 A | 12/1997 | Ravenscroft |
| 5,704,361 A | 1/1998 | Seward et al. |
| 5,713,949 A | 2/1998 | Jayaraman |
| 5,716,393 A | 2/1998 | Lindenberg et al. |
| 5,718,701 A | 2/1998 | Shai et al. |
| 5,720,735 A | 2/1998 | Dorros |
| 5,725,521 A | 3/1998 | Mueller |
| 5,725,547 A | 3/1998 | Chuter |
| 5,725,572 A | 3/1998 | Lam et al. |
| 5,728,068 A | 3/1998 | Leone et al. |
| 5,733,301 A | 3/1998 | Forman |
| 5,736,642 A | 4/1998 | Yost et al. |
| 5,741,234 A | 4/1998 | Aboul-Hosn |
| 5,741,333 A | 4/1998 | Frid |
| 5,746,767 A | 5/1998 | Smith |
| 5,752,518 A | 5/1998 | McGee et al. |
| 5,755,769 A | 5/1998 | Richard et al. |
| 5,755,778 A | 5/1998 | Kleshinski |
| 5,759,174 A | 6/1998 | Fischell et al. |
| 5,759,769 A | 6/1998 | Sia et al. |
| 5,762,638 A | 6/1998 | Shikani et al. |
| 5,779,642 A | 7/1998 | Nightengale |
| 5,782,762 A | 7/1998 | Vining |
| 5,792,119 A | 8/1998 | Marx |
| 5,795,325 A | 8/1998 | Valley et al. |
| 5,797,920 A | 8/1998 | Kim |
| 5,810,008 A | 9/1998 | Dekel et al. |
| 5,810,836 A | 9/1998 | Hussein et al. |
| 5,819,723 A | 10/1998 | Joseph |
| 5,824,046 A | 10/1998 | Smith et al. |
| 5,824,048 A | 10/1998 | Tuch |
| 5,830,191 A | 11/1998 | Hildwein et al. |
| 5,830,222 A | 11/1998 | Makower |
| 5,840,431 A | 11/1998 | Kall |
| 5,843,079 A | 12/1998 | Suslov |
| 5,843,158 A | 12/1998 | Lenker et al. |
| 5,843,175 A | 12/1998 | Frantzen |
| 5,846,205 A | 12/1998 | Curley et al. |
| 5,849,037 A | 12/1998 | Frid |
| 5,851,210 A | 12/1998 | Torossian |
| 5,855,597 A | 1/1999 | Jayaraman |
| 5,855,598 A | 1/1999 | Pinchuk |
| 5,860,920 A | 1/1999 | McGee et al. |
| 5,860,951 A | 1/1999 | Eggers et al. |
| 5,868,763 A | 2/1999 | Spence et al. |
| 5,868,777 A | 2/1999 | Lam |
| 5,873,904 A | 2/1999 | Ragheb et al. |
| 5,876,345 A | 3/1999 | Eaton et al. |
| 5,876,434 A | 3/1999 | Flomenblit et al. |
| 5,876,445 A | 3/1999 | Andersen et al. |
| 5,876,448 A | 3/1999 | Thompson et al. |
| 5,885,219 A | 3/1999 | Nightengale |
| 5,906,587 A | 5/1999 | Zimmon |
| 5,908,448 A | 6/1999 | Roberts et al. |
| 5,911,702 A | 6/1999 | Romley et al. |
| 5,916,158 A | 6/1999 | Webster, Jr. |
| 5,919,191 A | 7/1999 | Lennox et al. |
| 5,922,019 A | 7/1999 | Hankh et al. |
| 5,935,135 A | 8/1999 | Bramfitt et al. |
| 5,938,697 A | 8/1999 | Killion et al. |
| 5,951,567 A | 9/1999 | Javier, Jr. et al. |
| 5,954,636 A | 9/1999 | Schwartz et al. |
| 5,954,649 A | 9/1999 | Chia et al. |
| 5,957,849 A | 9/1999 | Munro |
| 5,957,919 A | 9/1999 | Laufer |
| 5,957,949 A | 9/1999 | Leonhardt et al. |
| 5,957,974 A | 9/1999 | Thompson et al. |
| 5,967,990 A | 10/1999 | Thierman et al. |
| 5,968,053 A | 10/1999 | Revelas |
| 5,968,070 A | 10/1999 | Bley et al. |
| 5,971,767 A | 10/1999 | Kaufman et al. |
| 5,971,980 A | 10/1999 | Sherman |
| 5,972,017 A | 10/1999 | Berg et al. |
| 5,976,178 A | 11/1999 | Goldsteen et al. |
| 5,984,871 A | 11/1999 | TenHoff et al. |
| 5,989,276 A | 11/1999 | Houser et al. |
| 5,993,484 A | 11/1999 | Shmulewitz |
| 6,001,124 A | 12/1999 | Bachinski |
| 6,002,955 A | 12/1999 | Willems et al. |
| 6,003,517 A | 12/1999 | Sheffield et al. |
| 6,004,269 A | 12/1999 | Crowley et al. |
| 6,004,273 A | 12/1999 | Sakamoto et al. |
| 6,004,319 A | 12/1999 | Goble et al. |
| 6,007,544 A | 12/1999 | Kim |
| 6,007,574 A | 12/1999 | Pulnev et al. |
| 6,010,529 A | 1/2000 | Herweck et al. |
| 6,011,995 A | 1/2000 | Guglielmi et al. |
| 6,013,033 A | 1/2000 | Berger et al. |
| 6,013,093 A | 1/2000 | Nott et al. |
| 6,013,854 A | 1/2000 | Moriuchi |
| 6,015,405 A | 1/2000 | Schwartz et al. |
| 6,019,787 A | 2/2000 | Richard et al. |
| 6,019,789 A | 2/2000 | Dinh et al. |
| 6,022,371 A | 2/2000 | Killion |
| 6,024,703 A | 2/2000 | Zanelli et al. |
| 6,024,756 A | 2/2000 | Huebsch et al. |
| 6,030,392 A | 2/2000 | Dakov |

(56) References Cited

U.S. PATENT DOCUMENTS

| | | |
|---|---|---|
| 6,032,674 A | 3/2000 | Eggers et al. |
| 6,036,702 A | 3/2000 | Bachinski et al. |
| 6,045,511 A | 4/2000 | Ott et al. |
| 6,045,532 A | 4/2000 | Eggers et al. |
| 6,048,362 A | 4/2000 | Berg |
| 6,053,940 A | 4/2000 | Wijay |
| 6,053,941 A | 4/2000 | Lindenberg et al. |
| 6,059,731 A | 5/2000 | Seward et al. |
| 6,059,811 A | 5/2000 | Pinchasik et al. |
| 6,063,111 A | 5/2000 | Hieshima et al. |
| 6,064,902 A | 5/2000 | Haissaguerre et al. |
| 6,066,169 A | 5/2000 | McGuinness |
| 6,068,638 A | 5/2000 | Makower |
| 6,070,094 A | 5/2000 | Swanson et al. |
| 6,074,349 A | 6/2000 | Crowley |
| 6,074,362 A | 6/2000 | Jang et al. |
| 6,074,416 A | 6/2000 | Berg et al. |
| 6,080,109 A | 6/2000 | Baker et al. |
| 6,080,182 A | 6/2000 | Shaw et al. |
| 6,083,162 A | 7/2000 | Vining |
| 6,096,053 A | 8/2000 | Bates |
| 6,099,563 A | 8/2000 | Zhong |
| 6,102,887 A | 8/2000 | Altman |
| 6,112,123 A | 8/2000 | Kelleher et al. |
| 6,113,612 A | 9/2000 | Swanson et al. |
| 6,117,101 A | 9/2000 | Diederich et al. |
| 6,120,432 A | 9/2000 | Sullivan et al. |
| 6,120,534 A | 9/2000 | Ruiz |
| 6,120,803 A | 9/2000 | Wong et al. |
| 6,124,523 A | 9/2000 | Banas et al. |
| 6,129,726 A | 10/2000 | Edwards et al. |
| 6,135,997 A | 10/2000 | Laufer et al. |
| 6,143,019 A | 11/2000 | Motamedi et al. |
| 6,152,937 A | 11/2000 | Peterson et al. |
| 6,152,945 A | 11/2000 | Bachinski et al. |
| 6,159,225 A | 12/2000 | Makower |
| 6,162,245 A | 12/2000 | Jayaraman |
| 6,165,127 A | 12/2000 | Crowley |
| 6,174,323 B1 | 1/2001 | Biggs et al. |
| 6,176,872 B1 | 1/2001 | Miksza |
| 6,181,348 B1 | 1/2001 | Geiger |
| 6,183,444 B1 | 2/2001 | Glines et al. |
| 6,186,942 B1 | 2/2001 | Sullivan et al. |
| 6,188,355 B1 | 2/2001 | Gilboa |
| 6,190,353 B1 | 2/2001 | Makower et al. |
| 6,200,313 B1 | 3/2001 | Abe et al. |
| 6,200,564 B1 | 3/2001 | Lamont et al. |
| 6,206,831 B1 | 3/2001 | Suorsa et al. |
| 6,226,543 B1 | 5/2001 | Gilboa et al. |
| 6,231,587 B1 | 5/2001 | Makower |
| 6,235,024 B1 | 5/2001 | Tu |
| 6,235,054 B1 | 5/2001 | Berg et al. |
| 6,239,705 B1 | 5/2001 | Glen |
| 6,241,742 B1 | 6/2001 | Spence et al. |
| 6,241,746 B1 | 6/2001 | Bosma et al. |
| 6,245,020 B1 | 6/2001 | Moore et al. |
| 6,245,057 B1 | 6/2001 | Sieben et al. |
| 6,245,102 B1 | 6/2001 | Jayaraman |
| 6,246,784 B1 | 6/2001 | Summers et al. |
| 6,254,632 B1 | 7/2001 | Wu et al. |
| 6,258,100 B1 | 7/2001 | Alferness et al. |
| 6,258,115 B1 | 7/2001 | Dubrul |
| 6,261,601 B1 | 7/2001 | Talwar et al. |
| 6,264,690 B1 | 7/2001 | Von Oepen |
| 6,270,515 B1 | 8/2001 | Linden et al. |
| 6,270,524 B1 | 8/2001 | Kim |
| 6,272,366 B1 | 8/2001 | Vining |
| 6,280,457 B1 | 8/2001 | Wallace et al. |
| 6,283,951 B1 | 9/2001 | Flaherty et al. |
| 6,283,983 B1 | 9/2001 | Makower et al. |
| 6,287,290 B1 | 9/2001 | Perkins et al. |
| 6,290,728 B1 | 9/2001 | Phelps et al. |
| 6,293,951 B1 | 9/2001 | Alferness et al. |
| 6,299,604 B1 | 10/2001 | Ragheb et al. |
| 6,299,635 B1 | 10/2001 | Frantzen |
| 6,306,096 B1 | 10/2001 | Seward et al. |
| 6,306,097 B1 | 10/2001 | Park et al. |
| 6,309,375 B1 | 10/2001 | Glines et al. |
| 6,309,415 B1 | 10/2001 | Pulnev et al. |
| 6,309,416 B1 | 10/2001 | Swanson et al. |
| 6,325,825 B1 | 12/2001 | Kula et al. |
| 6,328,689 B1 | 12/2001 | Gonzalez et al. |
| 6,331,116 B1 | 12/2001 | Kaufman et al. |
| 6,334,869 B1 | 1/2002 | Leonhardt et al. |
| 6,335,029 B1 | 1/2002 | Kamath et al. |
| 6,336,933 B1 | 1/2002 | Parodi |
| 6,342,591 B1 | 1/2002 | Zamora et al. |
| 6,343,936 B1 | 2/2002 | Kaufman et al. |
| 6,344,053 B1 | 2/2002 | Boneau |
| 6,346,940 B1 | 2/2002 | Fukunaga |
| 6,355,057 B1 | 3/2002 | DeMarais et al. |
| 6,371,964 B1 | 4/2002 | Vargas et al. |
| 6,379,382 B1 | 4/2002 | Yang |
| 6,380,732 B1 | 4/2002 | Gilboa |
| 6,391,036 B1 | 5/2002 | Berg et al. |
| 6,394,093 B1 | 5/2002 | Lethi |
| 6,394,956 B1 | 5/2002 | Chandrasekaran et al. |
| 6,409,686 B1 | 6/2002 | Guthrie et al. |
| 6,428,550 B1 | 8/2002 | Vargas et al. |
| 6,440,163 B1 | 8/2002 | Swanson et al. |
| 6,451,048 B1 | 9/2002 | Berg et al. |
| 6,458,153 B1 | 10/2002 | Bailey et al. |
| 6,466,687 B1 | 10/2002 | Uppaluri et al. |
| 6,488,673 B1 | 12/2002 | Laufer et al. |
| 6,490,474 B1 | 12/2002 | Willis et al. |
| 6,493,589 B1 | 12/2002 | Medhkour et al. |
| 6,505,065 B1 | 1/2003 | Yanof et al. |
| 6,506,408 B1 | 1/2003 | Palasis |
| 6,508,822 B1 | 1/2003 | Peterson et al. |
| 6,511,491 B2 | 1/2003 | Grudem et al. |
| 6,514,249 B1 | 2/2003 | Maguire et al. |
| 6,514,290 B1 | 2/2003 | Loomas |
| 6,516,213 B1 | 2/2003 | Nevo |
| 6,528,301 B1 | 3/2003 | Breme et al. |
| 6,533,812 B2 | 3/2003 | Swanson et al. |
| 6,551,302 B1 | 4/2003 | Rosinko et al. |
| 6,554,848 B2 | 4/2003 | Boylan et al. |
| 6,556,696 B1 | 4/2003 | Summers et al. |
| 6,558,333 B2 | 5/2003 | Gilboa et al. |
| 6,574,498 B1 | 6/2003 | Gilboa |
| 6,575,969 B1 | 6/2003 | Rittman et al. |
| 6,585,655 B2 | 7/2003 | Crowley |
| 6,593,884 B1 | 7/2003 | Gilboa et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,615,155 B2 | 9/2003 | Gilboa |
| 6,616,675 B1 | 9/2003 | Evard et al. |
| 6,620,176 B1 | 9/2003 | Peterson et al. |
| 6,623,437 B2 | 9/2003 | Hinchliffe et al. |
| 6,623,448 B2 | 9/2003 | Slater |
| 6,629,951 B2 | 10/2003 | Laufer et al. |
| 6,634,363 B1 | 10/2003 | Danek et al. |
| 6,635,279 B2 | 10/2003 | Kolter et al. |
| 6,635,281 B2 | 10/2003 | Wong et al. |
| 6,650,923 B1 | 11/2003 | Lesh et al. |
| 6,652,577 B2 | 11/2003 | Gianotti |
| 6,652,582 B1 | 11/2003 | Stinson |
| 6,660,015 B1 | 12/2003 | Berg et al. |
| 6,663,662 B2 | 12/2003 | Pacetti et al. |
| 6,667,051 B1 | 12/2003 | Gregory |
| 6,673,084 B1 | 1/2004 | Peterson et al. |
| 6,689,803 B2 | 2/2004 | Hunter |
| 6,692,494 B1 | 2/2004 | Cooper et al. |
| 6,694,163 B1 | 2/2004 | Vining |
| 6,695,859 B1 | 2/2004 | Golden et al. |
| 6,699,256 B1 | 3/2004 | Logan et al. |
| 6,702,780 B1 | 3/2004 | Gilboa et al. |
| 6,702,829 B2 | 3/2004 | Bachinski et al. |
| 6,711,429 B1 | 3/2004 | Gilboa et al. |
| 6,712,804 B2 | 3/2004 | Roue et al. |
| 6,712,812 B2 | 3/2004 | Roschak et al. |
| 6,712,845 B2 | 3/2004 | Hossainy |
| 6,719,698 B2 | 4/2004 | Manor et al. |

(56) References Cited

U.S. PATENT DOCUMENTS

| | | | |
|---|---|---|---|
| 6,719,781 B1 | 4/2004 | Kim | |
| 6,730,064 B2 | 5/2004 | Ragheb et al. | |
| 6,730,349 B2 | 5/2004 | Schwarz et al. | |
| 6,749,576 B2 | 6/2004 | Bauer | |
| 6,749,606 B2 | 6/2004 | Keast et al. | |
| 6,770,070 B1 | 8/2004 | Balbierz | |
| 6,773,457 B2 | 8/2004 | Ivancev et al. | |
| 6,785,410 B2 | 8/2004 | Vining et al. | |
| 6,790,228 B2 | 9/2004 | Hossainy et al. | |
| 6,819,785 B1 | 11/2004 | Vining et al. | |
| 6,829,379 B1 | 12/2004 | Knoplioch et al. | |
| 6,833,814 B2 | 12/2004 | Gilboa et al. | |
| 6,852,111 B1 | 2/2005 | Lieber | |
| 6,866,674 B2 | 3/2005 | Galdonik et al. | |
| 6,869,443 B2 | 3/2005 | Buscemi et al. | |
| 6,872,183 B2 | 3/2005 | Sampson et al. | |
| 6,886,558 B2 | 5/2005 | Tanaka | |
| 6,890,583 B2 | 5/2005 | Chudzik et al. | |
| 6,899,731 B2 | 5/2005 | Li et al. | |
| 6,909,913 B2 | 6/2005 | Vining | |
| 6,918,869 B2 | 7/2005 | Shaw et al. | |
| 6,918,927 B2 | 7/2005 | Bates et al. | |
| 6,920,882 B2 | 7/2005 | Berg et al. | |
| 6,929,637 B2 | 8/2005 | Gonzalez et al. | |
| 6,941,950 B2 | 9/2005 | Wilson et al. | |
| 6,960,219 B2 | 11/2005 | Grudem et al. | |
| 6,961,600 B2 | 11/2005 | Kohl et al. | |
| 6,970,733 B2 | 11/2005 | Willis et al. | |
| 6,994,713 B2 | 2/2006 | Berg et al. | |
| 6,996,430 B1 | 2/2006 | Gilboa et al. | |
| 6,997,189 B2 | 2/2006 | Biggs et al. | |
| 7,011,094 B2 | 3/2006 | Rapacki et al. | |
| 7,014,654 B2 | 3/2006 | Welsh et al. | |
| 7,022,088 B2 | 4/2006 | Keast et al. | |
| 7,086,398 B2 | 8/2006 | Tanaka | |
| 7,149,564 B2 | 12/2006 | Vining et al. | |
| 7,169,164 B2 | 1/2007 | Borillo et al. | |
| 7,175,644 B2 | 2/2007 | Cooper et al. | |
| 7,179,220 B2 | 2/2007 | Kukuk | |
| 7,191,101 B2 | 3/2007 | Knoplioch et al. | |
| 7,226,442 B2 | 6/2007 | Sheppard, Jr. et al. | |
| 7,226,472 B2 | 6/2007 | Pederson, Jr. et al. | |
| 7,232,409 B2 | 6/2007 | Hale et al. | |
| 7,236,620 B1 | 6/2007 | Gurcan | |
| 7,260,250 B2 | 8/2007 | Summers et al. | |
| 7,356,367 B2 | 4/2008 | Liang et al. | |
| 7,422,563 B2 | 9/2008 | Roschak et al. | |
| 7,481,775 B2 | 1/2009 | Weikel et al. | |
| 7,483,755 B2 | 1/2009 | Ingle et al. | |
| 7,517,320 B2 | 4/2009 | Wibowo et al. | |
| 7,815,590 B2 | 10/2010 | Cooper | |
| 7,963,925 B1 | 6/2011 | Schecter | |
| 7,985,187 B2 | 7/2011 | Wibowo et al. | |
| 8,235,908 B2 | 8/2012 | Roschak et al. | |
| 8,308,682 B2 | 11/2012 | Kramer et al. | |
| 8,337,516 B2 | 12/2012 | Escudero et al. | |
| 8,409,167 B2 * | 4/2013 | Roschak | 604/506 |
| 2001/0007940 A1 | 7/2001 | Tu et al. | |
| 2001/0021872 A1 | 9/2001 | Bailey et al. | |
| 2001/0026666 A1 | 10/2001 | Ferrera et al. | |
| 2001/0027339 A1 | 10/2001 | Boatman | |
| 2001/0027341 A1 | 10/2001 | Gianotti | |
| 2001/0044576 A1 | 11/2001 | Vining | |
| 2001/0044650 A1 | 11/2001 | Simso et al. | |
| 2001/0047180 A1 | 11/2001 | Grudem et al. | |
| 2001/0052344 A1 | 12/2001 | Doshi | |
| 2002/0002401 A1 | 1/2002 | McGuckin et al. | |
| 2002/0022833 A1 | 2/2002 | Maguire et al. | |
| 2002/0028006 A1 | 3/2002 | Novak et al. | |
| 2002/0028008 A1 | 3/2002 | Fan et al. | |
| 2002/0032477 A1 | 3/2002 | Helmus et al. | |
| 2002/0042564 A1 | 4/2002 | Cooper et al. | |
| 2002/0042565 A1 | 4/2002 | Cooper et al. | |
| 2002/0042622 A1 | 4/2002 | Vargas et al. | |
| 2002/0049370 A1 | 4/2002 | Laufer et al. | |
| 2002/0055772 A1 | 5/2002 | McGuckin et al. | |
| 2002/0071902 A1 | 6/2002 | Ding et al. | |
| 2002/0087153 A1 | 7/2002 | Roschak et al. | |
| 2002/0091433 A1 | 7/2002 | Ding et al. | |
| 2002/0111619 A1 | 8/2002 | Keast et al. | |
| 2002/0111620 A1 * | 8/2002 | Cooper et al. | 606/41 |
| 2002/0119178 A1 | 8/2002 | Levesque et al. | |
| 2002/0123786 A1 | 9/2002 | Gittings et al. | |
| 2002/0128647 A1 | 9/2002 | Roschak et al. | |
| 2002/0131625 A1 | 9/2002 | Vining et al. | |
| 2002/0133057 A1 | 9/2002 | Kukuk | |
| 2002/0138074 A1 | 9/2002 | Keast et al. | |
| 2002/0147462 A1 | 10/2002 | Mair | |
| 2002/0161321 A1 | 10/2002 | Sweezer et al. | |
| 2002/0161377 A1 | 10/2002 | Rabkin | |
| 2003/0017150 A1 | 1/2003 | Torphy | |
| 2003/0070676 A1 | 4/2003 | Cooper et al. | |
| 2003/0070682 A1 | 4/2003 | Wilson et al. | |
| 2003/0120292 A1 | 6/2003 | Park et al. | |
| 2003/0130657 A1 | 7/2003 | Tom et al. | |
| 2003/0153971 A1 | 8/2003 | Chandrasekaran | |
| 2003/0204138 A1 | 10/2003 | Choi | |
| 2003/0216806 A1 | 11/2003 | Togawa et al. | |
| 2004/0055606 A1 | 3/2004 | Hendricksen et al. | |
| 2004/0060563 A1 | 4/2004 | Rapacki et al. | |
| 2004/0073155 A1 | 4/2004 | Laufer et al. | |
| 2004/0073201 A1 | 4/2004 | Cooper et al. | |
| 2004/0073284 A1 | 4/2004 | Bates et al. | |
| 2004/0078054 A1 | 4/2004 | Biggs et al. | |
| 2004/0093070 A1 | 5/2004 | Hojeibane et al. | |
| 2004/0211434 A1 | 10/2004 | Loomas et al. | |
| 2004/0220556 A1 | 11/2004 | Cooper et al. | |
| 2004/0261203 A1 | 12/2004 | Dworzan | |
| 2005/0016530 A1 | 1/2005 | McCutcheon et al. | |
| 2005/0043751 A1 | 2/2005 | Phan et al. | |
| 2005/0043752 A1 | 2/2005 | Phan et al. | |
| 2005/0049615 A1 | 3/2005 | Cooper et al. | |
| 2005/0056292 A1 | 3/2005 | Cooper | |
| 2005/0060041 A1 | 3/2005 | Phan et al. | |
| 2005/0060042 A1 | 3/2005 | Phan et al. | |
| 2005/0060044 A1 | 3/2005 | Roschak et al. | |
| 2005/0085801 A1 | 4/2005 | Cooper et al. | |
| 2005/0096529 A1 | 5/2005 | Cooper et al. | |
| 2005/0107783 A1 | 5/2005 | Tom et al. | |
| 2005/0135662 A1 | 6/2005 | Vining et al. | |
| 2005/0137518 A1 | 6/2005 | Biggs et al. | |
| 2005/0137611 A1 | 6/2005 | Escudero et al. | |
| 2005/0137712 A1 | 6/2005 | Biggs et al. | |
| 2005/0137715 A1 | 6/2005 | Phan et al. | |
| 2005/0147284 A1 | 7/2005 | Vining et al. | |
| 2005/0165342 A1 | 7/2005 | Odland | |
| 2005/0171527 A1 | 8/2005 | Bhola | |
| 2005/0177144 A1 | 8/2005 | Phan et al. | |
| 2005/0182295 A1 | 8/2005 | Soper et al. | |
| 2005/0182475 A1 | 8/2005 | Jen et al. | |
| 2005/0192526 A1 | 9/2005 | Biggs et al. | |
| 2005/0228268 A1 | 10/2005 | Cole | |
| 2005/0251202 A1 | 11/2005 | Ewers et al. | |
| 2005/0261550 A1 | 11/2005 | Akimoto et al. | |
| 2005/0288549 A1 | 12/2005 | Mathis | |
| 2006/0023966 A1 | 2/2006 | Vining | |
| 2006/0116749 A1 | 6/2006 | Willink et al. | |
| 2006/0135984 A1 | 6/2006 | Kramer et al. | |
| 2006/0142672 A1 | 6/2006 | Keast et al. | |
| 2006/0183973 A1 | 8/2006 | Kamrava | |
| 2006/0254600 A1 | 11/2006 | Danek et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2007/0010438 A1 | 1/2007 | Mayo et al. | |
| 2007/0016072 A1 | 1/2007 | Grunwald et al. | |
| 2007/0092864 A1 | 4/2007 | Reinhardt et al. | |
| 2007/0123922 A1 | 5/2007 | Cooper et al. | |
| 2007/0255304 A1 | 11/2007 | Roschak et al. | |
| 2008/0009760 A1 | 1/2008 | Wibowo et al. | |
| 2008/0039715 A1 | 2/2008 | Wilson et al. | |
| 2008/0086107 A1 | 4/2008 | Roschak | |
| 2008/0097139 A1 | 4/2008 | Clerk et al. | |
| 2008/0213337 A1 | 9/2008 | Hermansson et al. | |

(56) References Cited

U.S. PATENT DOCUMENTS

| | | |
|---|---|---|
| 2008/0302359 A1 | 12/2008 | Loomas et al. |
| 2008/0312543 A1 | 12/2008 | Laufer et al. |
| 2009/0054805 A1 | 2/2009 | Boyle, Jr. |
| 2009/0076491 A1 | 3/2009 | Roschak et al. |
| 2009/0124883 A1 | 5/2009 | Wibowo et al. |
| 2009/0131765 A1 | 5/2009 | Roschak et al. |
| 2009/0143678 A1 | 6/2009 | Keast et al. |
| 2009/0204005 A1 | 8/2009 | Keast et al. |
| 2009/0275840 A1 | 11/2009 | Roschak et al. |
| 2009/0287087 A1 | 11/2009 | Gwerder et al. |
| 2009/0318904 A9 | 12/2009 | Cooper et al. |
| 2010/0268316 A1 | 10/2010 | Brenneman et al. |
| 2010/0305463 A1 | 12/2010 | Macklem et al. |
| 2010/0312141 A1 | 12/2010 | Keast et al. |
| 2011/0146673 A1 | 6/2011 | Keast et al. |
| 2011/0146674 A1 | 6/2011 | Roschak |
| 2011/0306997 A9 | 12/2011 | Roshak et al. |
| 2012/0085346 A9 | 4/2012 | Roschak |
| 2012/0089116 A9 | 4/2012 | Roschak |
| 2012/0123264 A9 | 5/2012 | Keast et al. |
| 2012/0289776 A1 | 11/2012 | Keast et al. |
| 2012/0289815 A1 | 11/2012 | Keast et al. |
| 2013/0041373 A1 | 2/2013 | Laufer |
| 2013/0046198 A1 | 2/2013 | Roschak et al. |
| 2013/0046296 A1 | 2/2013 | Laufer |
| 2013/0123638 A1 | 5/2013 | Tom et al. |
| 2013/0123826 A1 | 5/2013 | Kramer et al. |

FOREIGN PATENT DOCUMENTS

| | | |
|---|---|---|
| EP | 1151729 A1 | 11/2001 |
| EP | 1400204 A1 | 3/2004 |
| EP | 1485033 A2 | 12/2004 |
| WO | WO 87/05739 | 9/1987 |
| WO | WO 89/06515 | 7/1989 |
| WO | WO 90/01300 | 2/1990 |
| WO | WO 95/02361 | 1/1995 |
| WO | WO 95/32011 | 11/1995 |
| WO | WO 96/25886 | 8/1996 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 | 7/1998 |
| WO | WO 98/48706 | 11/1998 |
| WO | WO 98/57590 | 12/1998 |
| WO | WO 99/01076 | 1/1999 |
| WO | WO 99/11182 | 3/1999 |
| WO | WO 99/25419 | 5/1999 |
| WO | WO 99/38454 | 8/1999 |
| WO | WO 99/60953 | 12/1999 |
| WO | WO 00/21461 | 4/2000 |
| WO | WO 00/27313 | 5/2000 |
| WO | WO 00/45742 | 8/2000 |
| WO | WO 00/67825 | 11/2000 |
| WO | WO 00/72908 | 12/2000 |
| WO | WO 00/74579 | 12/2000 |
| WO | WO 01/10314 | 2/2001 |
| WO | WO 01/13839 | 3/2001 |
| WO | WO 01/28433 | 4/2001 |
| WO | WO 01/32088 | 5/2001 |
| WO | WO 01/39672 | 6/2001 |
| WO | WO 01/49213 | 7/2001 |
| WO | WO 01/54585 | 8/2001 |
| WO | WO 01/70117 | 9/2001 |
| WO | WO 01/74274 | 10/2001 |
| WO | WO 01/89366 | 11/2001 |
| WO | WO 02/00278 | 1/2002 |
| WO | WO 02/64045 | 8/2002 |
| WO | WO 02/64190 | 8/2002 |
| WO | WO 02/69823 | 9/2002 |
| WO | WO 03/020338 | 3/2003 |
| WO | WO 03/071924 | 9/2003 |
| WO | WO 03/073358 | 9/2003 |
| WO | WO 03/088820 | 10/2003 |
| WO | WO 03/097153 | 11/2003 |
| WO | WO 03/103479 | 12/2003 |
| WO | WO 2005/006963 | 1/2005 |
| WO | WO 2005/006964 | 1/2005 |
| WO | WO 2006/014731 | 2/2006 |
| WO | WO 2006/014732 | 2/2006 |
| WO | WO 2006/130821 | 12/2006 |
| WO | WO 2006/130873 | 12/2006 |
| WO | WO 2007/062406 | 5/2007 |
| WO | WO 2008/063935 | 5/2008 |
| WO | WO 2008/109760 | 9/2008 |

OTHER PUBLICATIONS

Choong, C., et al., "Prolongaton of patency of airway bypass stents with use of drug-eluting stents," *J. Thorac. Cardiovasc. Surg.*, 131:60-64, 2006.

Cordis Johnson & Johnson Gateway LLC: Bx Velocity Stent. Viewed at: http://www.jnjgateway.com/home.jhtm?loc=USENG&page=viewContent&contentId=fc0de00100001015&parentId=fcde00100001015&specialty=Circulatory_Disease_Management&category=Cardiac_Diagnosis_Interventions&subcategory=Stents_Balloon_Expandable Viewed on Sep. 5, 2002, 4 pages (please note p. 4 of 4 is blank).

Lausberg, H., et al., "Bronchial fenestraton improves expiratory flow in emphysematous human lungs," Ann. Thorac. Surg., 75:393-398, 2003.

Macklem, P., "Collateral ventilation," *N. Engl. J. Med.*, 298(1):49-50, 1978.

Panettieri, R., "Chronic Obstructive Pulmonary Disease," *Lippincott's Pathophysiology Series: Pulmonary Pathophysiology*, pp. 93-107, Grippi, M., et al., eds., J.B. Lippincott Company, Philadelphia, PA, 1995.

Pulmonary and Critical Care Medicine. Interventional Bronchoscopy with Stent Implant: Stents. Viewed at: http://view.vcu.edu/pulm-ccm/stents.htm Viewed on Aug. 26, 2002. 2 pages.

Rendina, E., et al., "Feasibility and safety of the airway bypass procedure for patients with emphysema," *J. Thorac. Cardiovasc. Surg.*, 125:1294-1299, 2003.

Terry, P., et al., "Collateral Ventilation in Man," *The New England Journal of Medicine*, 298(1):10-15, 1978.

Fessler, H., "Collateral Ventilation, the Bane of Bronchoscopic Volume Reduction," *Am J. Respir Crit. Care Med.* (editorial), 171:423-425, 2005.

Flenley, D., et al., "Factors Affecting Gas Exchange by Collateral Ventilation in the Dog," *Respiration Physiology*, 15:52-69, 1972.

Hogg, W., et al., "Gas Diffusion Across Collateral Channels," *Journal of Applied Physiology*, 33(5):568-575.

Menkes, H., et al., "Influence of Surface Forces on Collateral Ventilation," *Journal of Applied Physiology*, 31(4):544-549, 1971.

Wagner, E., et al., "Direct Assessment of Small Airways Reactivity in Human Subjects," *Am. J. Respir. Crit. Care Med.*, 157:447-452, 1998.

Woolcock, A., et al., "Mechanical Factors Influencing Collateral Ventilation in Human, Dog and Pig Lungs," *Journal of Applied Physiology*, 30(1):99-115, 1971.

\* cited by examiner

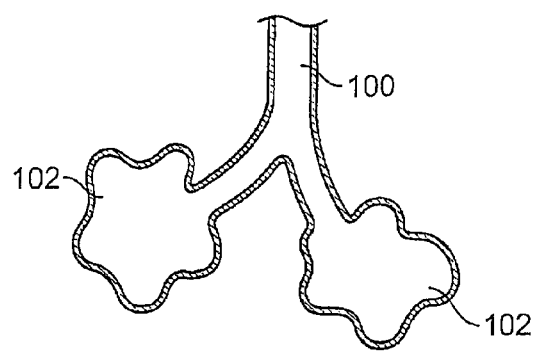
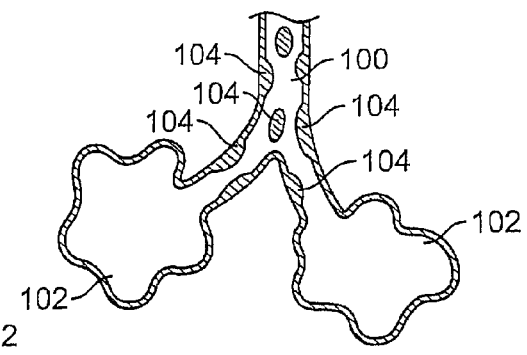
FIG. 1A　　　　　FIG. 1B
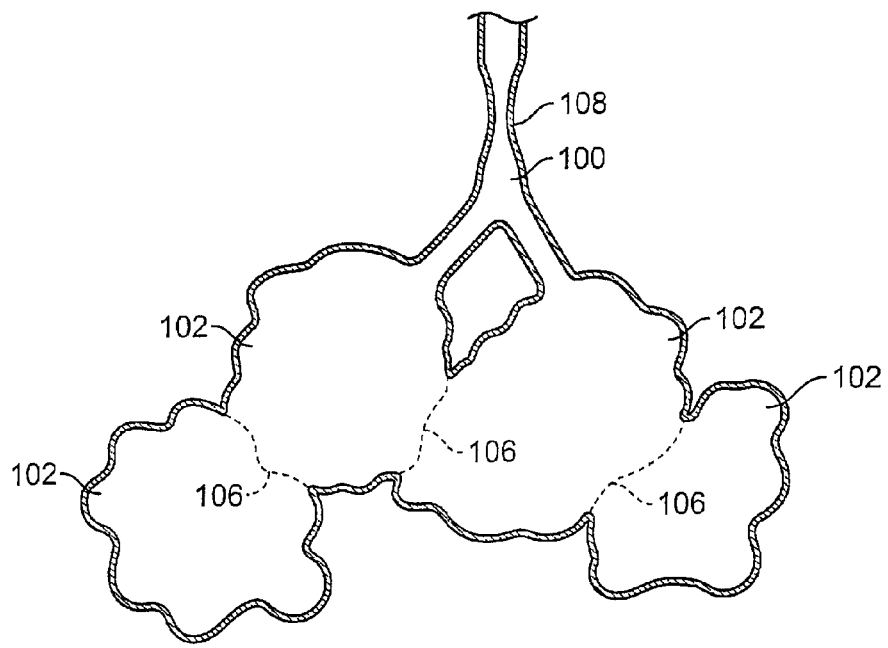
FIG. 1C

DEVICES FOR DELIVERING SUBSTANCES THROUGH AN EXTRA-ANATOMIC OPENING CREATED IN AN AIRWAY

CROSS REFERENCE TO RELATED APPLICATIONS

This application is a continuation of U.S. patent application Ser. No. 12/939,968, filed on Nov. 4, 2010, now U.S. Pat. No. 8,608,724, which is a continuation of U.S. patent application Ser. No. 11/538,950, filed Oct. 5, 2006, now U.S. Pat. No. 8,409,167, which is a continuation-in-part of U.S. patent application Ser. No. 10/895,022 filed Jul. 19, 2004, now abandoned.

FIELD OF THE INVENTION

This is directed to methods and devices for treating lungs. The methods and devices create channels, also known as extra-anatomic openings, in airways. Maintaining the patency of the channels allows air to pass directly out of the lung tissue which facilitates the exchange of oxygen ultimately into the blood and/or decompresses hyper-inflated lungs. In an additional variation, the channels provide access points for improved targeted delivery of medications or other substances to parenchymal lung tissue.

BACKGROUND OF THE INVENTION

It was found that creation of collateral channels in chronic obstructive pulmonary disease (COPD) patients allowed expired air to pass out of the lungs and decompressed hyperinflated lungs. Such methods and devices for creating and maintaining collateral channels are discussed in U.S. patent application Ser. No. 09/633,651, filed on Aug. 7, 2000; U.S. patent application Ser. Nos. 09/947,144, 09/946,706, and 09/947,126 all filed on Sep. 4, 2001; U.S. Provisional Application No. 60/317,338 filed on Sep. 4, 2001; U.S. Provisional Application No. 60/334,642 filed on Nov. 29, 2001; U.S. Provisional Application No. 60/367,436 filed on Mar. 20, 2002; and U.S. Provisional Application No. 60/374,022 filed on Apr. 19, 2002 each of which is incorporated by reference herein in its entirety.

The creation of these collateral channels or extra-anatomic openings also provide convenient access points to the lung parenchyma for delivery of substances to treat diseased tissue that may reside within the lung. The use of such openings allows for treatment in a minimally invasive manner and efficiently delivering needed substances to the desired area.

SUMMARY OF THE INVENTION

The invention includes methods and devices for treating a lung. The method includes treating diseased lung tissue by identifying a region in a lung having the diseased lung tissue, selecting a target site at an airway wall, creating an extra-anatomic opening at the target site; and delivering a substance through the extra-anatomic opening to treat the diseased tissue. In most cases, the diseased tissue is present beyond the wall of the airway and in the parenchymal tissue of the lung.

As discussed herein the method may or may not include placement of an implant. For example, the substance may or may not be delivered through the implant. Moreover, the conduit may be subsequently removed from the airway after the diseased tissue is sufficiently treated. The treatment may treat regions of destroyed tissue and trapped gasses by inducing a collapse of the tissue. Alternatively, or in combination, the treatment may be directed towards tumors or other conditions of the lung.

The methods relating to identifying regions of tissue, selecting a target site, avoidance of blood vessels, and creation of the extra-anatomic opening may rely on the teachings discussed herein that are suited to creation of a collateral opening for releasing trapped gasses.

The substance may be delivered using any catheter capable of being deployed in the lungs. The method may include advancing a delivery catheter into the lungs to deliver the substance. Alternatively, or in combination, the substance may be delivered using the devices described below.

The method also includes identifying the areas of the diseased tissue using the modes described herein or other modes that are suited for the particular medical condition in question. For example, a site for treating a tumor may be located using such means that are well suited for tumor identification.

Turning now to the methods and devices for selecting sites and creating openings, in one variation, the invention includes a method comprising selecting a treatment site in an airway of the lung, creating a hole in an airway wall of the airway; and expanding the hole in the airway wall.

Selecting the treatment site may include visual inspection of the site or inspection for the presence or absence of a blood vessel underneath the surface of the airway wall.

Selection of the site may be performed or aided by non-invasive imaging. Such imaging may include visual inspection, x-ray, ultrasound, Doppler, acoustic, MRI, PET, and computed tomography (CT) scans. Furthermore, a substance may be administered into the lungs to assist in the selection of the treatment site. For example, the substance may comprise a hyperpolarized gas, a thermochromatic dye, a regular dye, and/or a contrast agent.

Variations of the invention include the use of a less-traumatic holemaker for creation of the channel (note that a channel includes a hole that is created and subsequently expanded.) The less traumatic holemaker may include a piercing member (e.g., a needle, a cannula, a blade, a tube, a rod or other similar structure). The less traumatic holemaker may also include devices which minimize the collateral damage to tissue (e.g., low temperature RF devices, pulsating RF, low temperature laser, ultrasound, high pressure water, etc.)

In particular, the devices and methods prevent closure of the channel such that air may flow through the channel and into the airway. Such channels may be made by a variety of methods as discussed in the patents incorporated by reference above. For example, the channel may be made via a surgical incision, a needle, a rotary coring device, etc. Furthermore, the channel may be made by an energy based device, e.g., RF device, laser, etc. However, it has been noted that use of low temperature devices, e.g., mechanical devices, to create the channel result in less trauma to surrounding tissue and thereby minimize the healing response of the tissue. Accordingly, such modes of creating the channel often result in less occlusion of the channel.

The method includes expanding the hole by inserting a conduit into the hole. Furthermore, the method may comprise partially expanding the hole by deploying the conduit in the hole, and then fully expanding the hole by expanding the conduit within the hole.

Preventing closure may be performed using various approaches including, but not limited to, biochemical, electrical, thermal, irradiation, or mechanical approaches (or any combination thereof).

The method may also include delivering a bio-active composition, as described herein, to maintain patency of the channel or conduit. The bio-active composition may be delivered to the airway wall prior to creation of the channel, subsequent to creation of the channel, and/or after insertion and deployment of the conduit. The bio-active composition may also be delivered through a drug eluting process, either through a composition placed on the conduit, or via delivery of a separate eluting substance.

Biochemical approaches include delivery of medicines that inhibit closure of the surgically created channel. The medicines may be delivered locally or systematically. In one variation, a delivery catheter includes a dispense lumen that sends a drug to the target site. Also, bioactive substances may be delivered to the channel tissue using various delivery vehicles such as a conduit. The bioactive substance may be disposed on an exterior surface of the conduit such that it interacts with the channel tissue when the conduit is placed at the injury site. Also, bioactive substances may be delivered to the channel tissue before or after the conduit is positioned in the channel. The bioactive agent may also be delivered to the target site alone. That is, a medicine may be sent to the surgically created channel as the sole mechanism for maintaining the patency of the channel.

Also, systematic delivery of medicines may be carried out through digestion, injection, inhalation, etc. Systematic delivery of medicines may be provided alone or in combination with other techniques described herein. For example, a patient having undergone the procedures described herein may be prescribed steroids and/or COX-2 inhibitors in an attempt to prolong the effects of the treatment.

Any of the conduits discussed herein may also include at least one visualization feature disposed on a portion of the tissue barrier. The visualization feature may be a stripe circumferentially disposed about at least a portion of the center section. The visualization feature serves to aid in placement or deployment of the conduit in a target site.

Another conduit for maintaining the patency of a channel created in tissue comprises a radially expandable center section and extension members as described above. A bioactive substance is disposed on at least a portion of a surface of the conduit. Also, when the conduit is radially expanded it has an overall length and an inner diameter such that a ratio of the overall length to the inner diameter ranges from 1/6 to 2/1. The conduit may also be provided such that this ratio ranges from 1/4 to 1/1 and perhaps, 1/4 to 1/2. A tissue barrier may be disposed on at least a portion of the exterior surface corresponding to the center section. The tissue barrier may be comprised of various materials including but not limited to polymers and elastomers. An example of a material which may be used for the tissue barrier is silicone. Additional matrixes of biodegradable polymer and medicines may be associated with the tissue barrier such that controlled doses of medicines are delivered to the tissue opening.

The invention includes a hole-making catheter for creating and dilating an opening within tissue, the catheter comprising an elongate shaft having a proximal portion and a distal portion, and at least one lumen extending through the proximal end; a balloon having an interior in fluid communication with the lumen, the balloon located on the distal portion of the elongate shaft, the balloon having an uninflated state and an inflated state; a piercing member located at the distal portion of the elongate shaft, the piercing member being extendable and retractable within the elongate shaft; and a depth limiter stop located on the exterior of the distal portion of the elongate shaft, proximal to the balloon and larger in working diameter than the uninflated balloon, which limits the maximum penetration of the catheter into tissue.

The piercing member may include a body portion having a lumen extending therethrough. The lumen of the piercing member may be in fluid communication with a central lumen of the elongate shaft. In some variations of the invention an obturator is used within the device, where the obturator is slidably located within the lumen of the elongate body and piercing member.

The elongate body and/or piercing member may have multiple lumens. For example, they may be constructed from multi-lumen tubing. In some variations, the piercing member is retractable within the elongate shaft.

The balloon member may consist of a distensible balloon or a non-distendsible balloon. For either type of balloon, the working diameter may closely match the outer diameter of the piercing member.

The invention may also include an implant located about the balloon of the device. In use, the piercing member would create a channel within the tissue, the device is then further advanced until the implant is located within the channel. Inflation of the balloon then deploys the implant within the channel thereby improving the patency of the channel.

Implants for the present invention include, but are not limited to, a stent, conduit, grommet, valve, graft, anchor, etc.

It should be noted that since the device must often access airways deep within the lung, the elongate shaft may be comprised of a flexible material. In particular, the elongate shaft may be sufficiently flexible to pass through a fully articulated bronchoscope.

The piercing member of the current invention may also be used to deliver bio-active agents to the site of the collateral channel. As described herein, such agents may increase the duration of patency of the channels and/or implants.

The invention includes a balloon catheter for deploying a device within an opening in tissue, the balloon catheter comprising an elongate shaft having a proximal portion, a distal portion, a proximal end, a distal end; and at least one lumen extending through the proximal end, a balloon having an interior in fluid communication with the lumen, the balloon located on the distal end portion of the elongate shaft, a guide member extending distally from the distal end of the elongate shaft, the guide member comprising a rounded surface at an end opposite to the elongate shaft, where the guide member has sufficient column strength to penetrate the opening in tissue, the guide member further comprising at least one resistance surface a such that when the body enters the opening, the resistance surface exerts resistance against tissue upon removal of the guide member from the opening.

The resistance surface may have an increased diameter greater to provide resistance upon removal from tissue. It may alternatively, or in combination, comprise a rough surface to provide added friction upon removal of the device.

The guide member may be tapered, rounded, partially-spherical, elliptical, prolate, cone-shaped, triangular, or any similar shape. It is contemplated that there may be more than one resistance surface on the guide body. Moreover, the guide body may have a wavy/variable diameter shape providing several resistance surfaces on the areas of increased diameter.

The device may also be used with an implant that may be located about the balloon where upon expansion of the balloon, the implant deploys. The implant may be selected from a stent, conduit, grommet, valve, graft, and anchor.

In another variation of the invention, the balloon catheter may further comprise a dilating member located distally of the balloon. The dilating member may be is located on the distal portion of the shaft between the distal end and the balloon and may comprise a tapered section, a second balloon, or other similar structure.

In some variations of the invention, the dilating member may be retractable within the elongate shaft.

The device may also include a needle assembly moveably located in the instrument lumen, where the needle assembly is advanceable through a hole-making lumen and out of the opening in the rounded surface.

The balloon catheter may be constructed to be sufficient flexibility to advance through a fully articulated bronchoscope.

The balloon catheter may also be configured to deliver bio-active substances (e.g., drugs, medicines, compounds, etc.) to the tissue, either via the elongate tube or the guide member. Furthermore, the device may be adapted to provide suction to clear the target site.

The invention includes a hole-making catheter for creating and dilating an opening within tissue, the catheter comprising; an elongate shaft having a proximal portion and a distal portion, and at least one lumen extending through the proximal end; a nondistensible balloon having an interior in fluid communication with the lumen, the nondistensible balloon located on the distal portion of the elongate shaft; and a piercing member located at the distal portion of the elongate shaft, the piercing member being extendable and retractable within the elongate shaft.

The invention includes an implant delivery system for deploying the implant within a wall of tissue, the system comprising; an elongate shaft having a distal portion, a proximal end, a distal end, at least one lumen extending through the proximal end; a balloon member having an interior in fluid communication with the lumen, the balloon member located on the distal portion of the elongate shaft; a piercing member distally located to the distal end of the elongate shaft within the second lumen, the solid piercing member having a sharpened distal end adapted to penetrate tissue; and an expandable implant located about the balloon member.

The preceding illustrations are examples of the invention described herein. It is contemplated that, where possible, combinations of features/aspects of specific embodiments or combinations of the specific embodiments themselves are within the scope of this disclosure.

This application is also related to the following applications 60/420,440 filed Oct. 21, 2002; 60/387,163 filed Jun. 7, 2002; Ser. No. 10/235,240 filed Sep. 4, 2002; Ser. No. 09/947, 144 filed Sep. 4, 2001; Ser. No. 09/908,177 filed Jul. 18, 2001; Ser. No. 09/633,651 filed Aug. 7, 2000; and 60/176,141 filed Jan. 14, 2000; Ser. No. 10/080,344 filed Feb. 21, 2002; Ser. No. 10/079,605 filed Feb. 21, 2002; Ser. No. 10/280,851 filed Oct. 25, 2002; and Ser. No. 10/458,085 filed Jun. 9, 2003. Each of which is incorporated by reference herein.

BRIEF DESCRIPTION OF THE DRAWINGS

FIGS. 1A-1C illustrate various states of the natural airways and the blood-gas interface.

DETAILED DESCRIPTION OF THE INVENTION

Figure 1D:
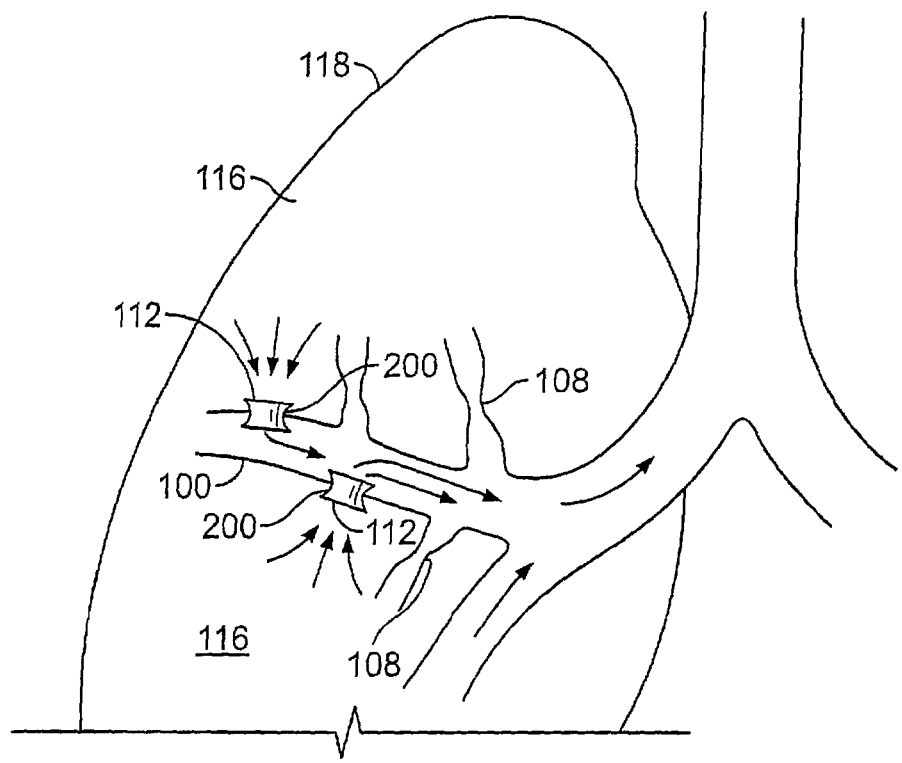
FIG. 1D illustrates a schematic of a lung demonstrating a principle of the invention described herein.

Described herein are devices (and methods) for treating diseased lung tissue. In particular, methods and devices are described that serve to maintain collateral openings or channels through an airway wall so that air is able to pass directly out of the lung tissue and into the airways or so that substances may be delivered to parenchymal tissue beyond the airways but within the lungs.

By "channel" it is meant to include, but not be limited to, any opening, hole, slit, channel or passage created in the tissue wall (e.g., airway wall). The channel may be created in tissue having a discrete wall thickness and the channel may extend all the way through the wall. Also, a channel may extend through lung tissue which does not have well defined boundaries such as, for example, parenchymal tissue.

The channels may be maintained by preventing or inhibiting tissue from growing into or otherwise blocking the channel. Chemical, electrical, light, mechanical, or a combination of any two or more of these approaches may be performed to maintain the channel openings. For example, the channel walls may be treated with a bioactive agent which inhibits tissue growth. The bioactive agent may be delivered locally or systematically. Also, the channels may be treated with rf energy, heat, electrical energy, or radiation to inhibit tissue overgrowth. These treatments may be performed once, periodically, or in response to the severity of the channel blockage. For example, the tissue blockage may be periodically removed with a laser or another tissue-removal tool. Also, mechanical devices and instruments may be deployed in the channel to prevent tissue growth from blocking the channel.

Mechanical devices include without limitation conduits, valves, sponges, etc. These mechanical devices may be deployed permanently or temporarily. If deployed temporarily, the devices are preferably left in the channel for a sufficient amount of time such that the channel tissue heals coaxially around the device if the medical practitioner intends to create a permanent opening in the airway wall.

FIGS. 1A-1C are simplified illustrations of various states of a natural airway and a blood gas interface found at a distal end of those airways. FIG. 1A shows a natural airway 100 which eventually branches to a blood gas interface 102.

Although not shown, the airway comprises an internal layer of epithelial pseudostratified columnar or cuboidal cells. Mucous secreting goblet cells are also found in this layer and cilia may be present on the free surface of the epithelial lining of the upper respiratory airways. Supporting the epithelium is a loose fibrous, glandular, vascular lamina propria including mobile fibroblasts. Deep in this connective tissue layer is supportive cartilage for the bronchi and smooth muscle for the bronchi and bronchioles.

FIG. 1B illustrates an airway 100 and blood gas interface 102 in an individual having COPD. The obstructions 104 impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A-1C. Often, the states of the lung depicted in FIGS. 1B and 1C may be found in the same lung.

FIG. 1D illustrates airflow in a lung 118 when conduits 200 are placed in collateral channels 112. As shown, collateral channels 112 (located in an airway wall) place lung tissue 116 in fluid communication with airways 100 allowing air to pass directly out of the airways 100 whereas constricted airways 108 may ordinarily prevent air from exiting the lung tissue 116. While the invention is not limited to the number of collateral channels which may be created, it is to be understood that 1 or 2 channels may be placed per lobe of the lung and perhaps, 2-12 channels per individual patient. However, as stated above, the invention includes the creation of any number of collateral channels in the lung. This number may vary on a case by case basis. For instance, in some cases in an emphysematous lung, it may be desirable to place 3 or more collateral channels in one or more lobes of the lung.

Although FIG. 1D depicts a mechanical approach to maintaining channels in the airway walls, the channel openings may be maintained using a variety of approaches or combinations of approaches.

As shown in FIGS. 2A-2G, the conduits described herein generally include a center section 208 and at least one extension member (or finger) 202 extending from each end of the center section. The extension members, as will be discussed in more detail below, are capable of deflecting or outwardly bending to secure the conduit in an opening created in an airway wall thereby maintaining the patency of the opening. The extension members may deflect such that opposing extension members may form a V, U or other type of shape when viewed from the side.

Additionally, the conduits shown in FIGS. 2A-2G include a center-control segment 235, 256 which restricts or limits radial expansion of the center section. The center-control segments are adapted to straighten as the center section is radially expanded. Once the center-control segments become straight or nearly straight, radial expansion of the conduit is prevented. In this manner, the radial expansion of the conduit may be self controlled.

It is understood that the conduits discussed herein are not limited to those shown in the figures. Instead, conduits of various configurations may be used as described herein. Such conduits are described in the following patent application Ser. No. 09/908,177 filed Jul. 18, 2001; PCT/U.S. Ser. No. 03/12323 filed Apr. 21, 2003; Ser. No. 09/947,144 filed Sep. 4, 2001; Ser. No. 10/235,240 filed Sep. 4, 2002; and Ser. No. 10/458,085 filed Jun. 9, 2003 the entirety of each of which is hereby incorporated by reference.

Conduit States

The conduits described herein may have various states (configurations or profiles) including but not limited to (1.) an undeployed state and (2.) a deployed state.

Figure 2A:
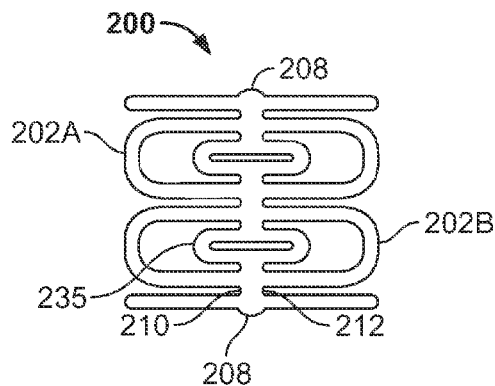
FIG. 2A illustrates a side view of a conduit in an undeployed state.

The undeployed state is the configuration of the conduit when it is not secured in an opening in an airway wall and, in particular, when its extension members (or fingers) are not outwardly deflected to engage the airway wall. FIG. 2A is a side view of a conduit 200 in an undeployed state. As shown in this figure, extension members 202A, 202B extend straight from the ends 210, 212 respectively of center section 208. The extension members shown in this example are parallel. However, the invention is not so limited and the extension members need not be parallel.

Figure 2B:
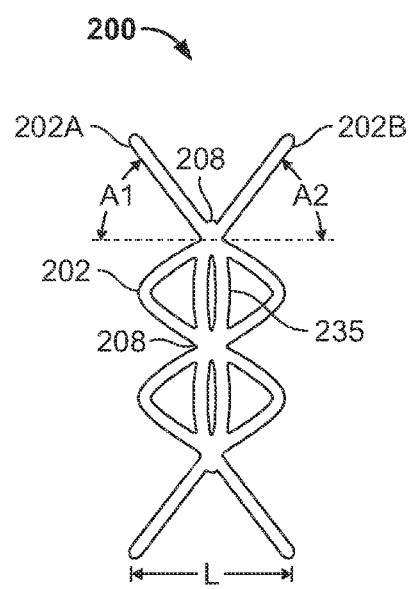
FIG. 2B illustrates a side view of the conduit of FIG. 2A shown in a deployed shape.
Figure 2D:
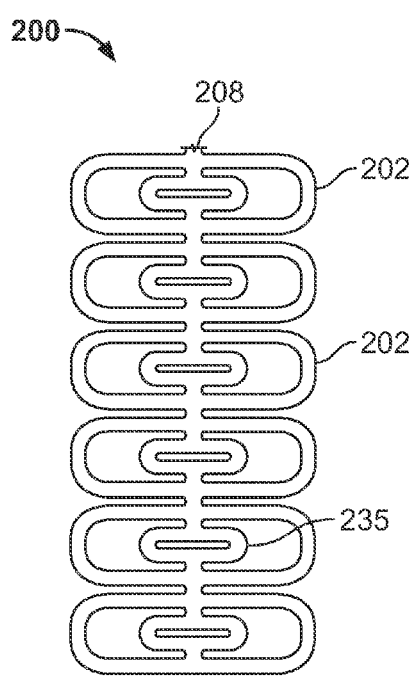
FIG. 2D is a cylindrical projection of the undeployed conduit shown in FIG. 2A.
Figure 2C:
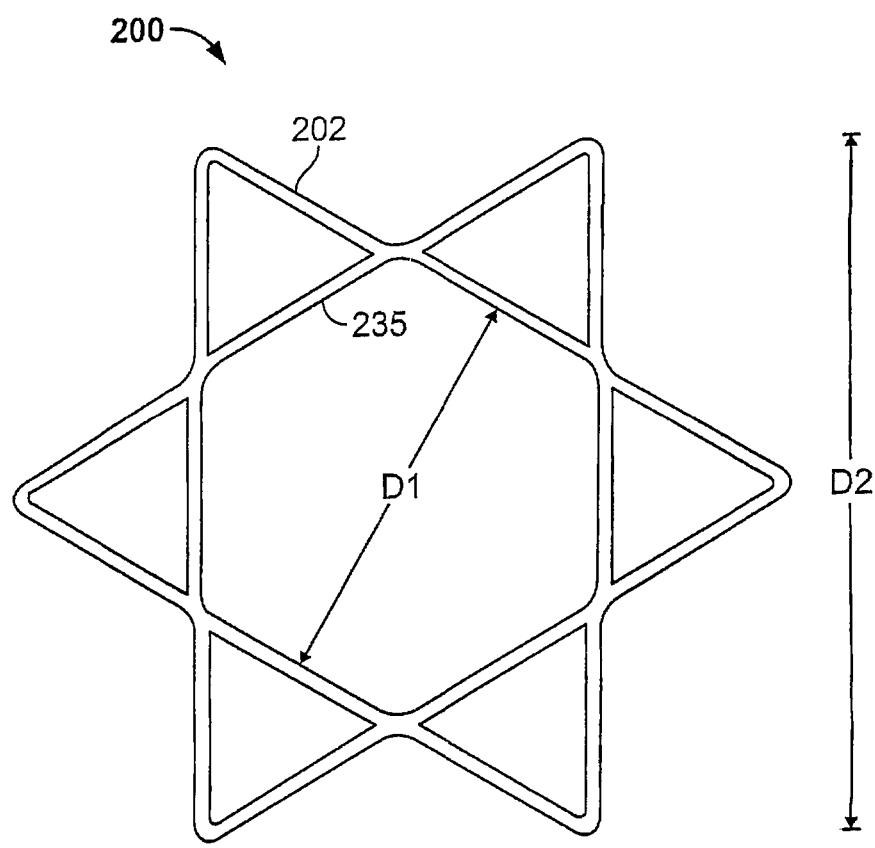
FIG. 2C illustrates a front view of the conduit shown in FIG. 2B.

The deployed state is the configuration of the conduit when it is secured in a channel created in an airway wall and, in particular, when its extension members are outwardly bent to engage the airway wall such that the conduit is fixed in the opening. An example of a conduit in its deployed configuration is shown in FIGS. 2B and 2C. FIG. 2B is a side view of a conduit in its deployed state and FIG. 2C shows a front view of the conduit of FIG. 2B.

Center Section of the Conduit

As shown in FIGS. 2A-2D, the conduit includes a center section 208 having a short passageway. This center section may be a tubular-shaped open-frame (or mesh) structure having a plurality of ribs. Also, as explained in more detail below, the center section may be a sheet of material.

The axial length of the center section or passageway may be relatively short. In FIGS. 2A-2D, the passageway's length is about equal to the width of a wire segment or rib. Here, the center section serves as a bridge or junction for the extension members and it is not required to be long. The axial length of the passageway may therefore be less than 1 mm and even approach 0 mm. In one example, the length of the center section is less than twice the square root of a cross sectional area of the center section. However, the center section may also have passageways which have lengths greater than 1 mm.

The overall length (L) of the conduit may be distinguished from the length of the center section because the overall length includes the lengths of the extension members. Further, the overall length (L) is dependent on which state the conduit is in. The overall length of the conduit will typically be shorter when it is in a deployed state as shown in FIG. 2B than when it is in an undeployed state as shown in FIG. 2A. The overall length (L) for a deployed conduit may be less than 6 mm and perhaps, between 1 and 20 mm.

FIG. 2C shows a front view of the conduit 200 shown in FIG. 2B. FIG. 2C shows the passageway having a hexagonal (or circular) cross section. The cross-section, however, is not so limited. The cross section may be circular, oval, rectangular, elliptical, or any other multi-faceted or curved shape. The inner diameter ($D_1$) of the center section, when deployed, may range from 1 to 10 mm and perhaps, from 2 to 5 mm. Moreover, in some variations, the cross-sectional area of the passageway, when deployed, may be between 0.2 mm² to 300 mm² and perhaps between 3 mm² and 20 mm²

The diameter of the center section, when deployed, thus may be significantly larger than the passageway's axial length (e.g., a 3 mm diameter and an axial length of less than 1 mm). This ratio of the center section length to diameter (D1) may range from about 0:10 to 10:1, 0.1:6 to 2:1 and perhaps from 1:2 to 1:1.

The diameter of the center section, when deployed, may also be nearly equal to the overall length (L) of the conduit 200. This overall length (L) to diameter (D1) ratio may range from 1:10 to 10:1, 1:6 to 2:1, and perhaps from 1:4 to 1:1. However, the invention is not limited to any particular dimensions or ratio unless so indicated in the appended claims. Rather, the conduit should have a center section such that it can maintain the patency of a collateral channel in an airway wall. The dimensions of the center section (and the conduit as a whole) may be chosen based on the tissue dimensions. When the channel is long in its axial length, for example, the length of the center section may likewise be long or identical to the channel's length.

Extension Members of the Conduit

As mentioned above, extending from the ends of the center section 208 are extension members 202A, 202B which, when the conduit is deployed, form angles A1, A2 with a central axis of the passageway. When viewed from the side such as in FIG. 2B, opposing extension members may have a V, U, or other shape. The extension members 202A, 202B may thus outwardly rotate until they sandwich tissue (not shown) between opposing extension members.

The angles A1, A2 may vary and may range from, for example, 30 to 150 degrees, 45 to 135 degrees and perhaps from 30 to 90 degrees. Opposing extension members may thus form angles A1 and A2 of less than 90 degrees when the conduit is deployed in a channel. For example, angles A1 and A2 may range from 30 to 60 degrees when the conduit is deployed.

The conduits of the present invention are effective and may maintain a surgically created opening despite not substantially sandwiching tissue between opposing extension members as described above. Additionally, it is not necessary for the conduits of the present invention to prevent air from flowing along the exterior of the conduit. That is, air may move into (and through) spaces between the exterior of the conduit and the interior wall of the tissue channel. Thus, fluidly sealing the edges of the conduit to prevent side flow or leakage around the conduit is not crucial for the conduits to be effective. However, the conduits of the present invention are not so limited and may reduce or eliminate side flow by, for example, increasing the angles A1 and A2 and adding sealant around the exterior of the conduit.

Moreover, the angle A1 may be different than angle A2. Accordingly, the conduit may include proximal extension members which are parallel (or not parallel) to the distal extension members. Additionally, the angle corresponding to each proximal extension member may be different or identical to that of another proximal extension member. Likewise, the angle corresponding to each distal extension member may be different or identical to that of another distal extension member.

The extension members may have a length between 1 and 20 mm and perhaps, between 2 and 6 mm. Also, with reference to FIG. 2C, the outer diameter ($D_2$) of a circle formed by the free ends of the extension members may range from 2 to 20 and perhaps, 3 to 10 mm. However, the invention is not limited to the dimensions disclosed above. Furthermore, the length of the distal extension members may be different than the length of the proximal extension members. The length of the distal extension members may be, for example, longer than that of the proximal extension members. Also, the lengths of each proximal extension member may be different or identical to that of the other proximal extension members. Likewise, the lengths of each distal extension member may be different or identical to that of the other distal extension members.

The number of extension members on each end of the center section may also vary. The number of extension members on each end may range from 2-10 and perhaps, 3-6. Also, the number of proximal extension members may differ from the number of distal extension members for a particular conduit. Moreover, the extension members may be symmetrical or non-symmetrical about the center section. The proximal and distal extension members may also be arranged in an in-line pattern or an alternating pattern. The extension members or the center section may also contain barbs or other similar configurations to increase adhesion between the conduit and the tissue. The extension members may also have openings to permit tissue ingrowth for improved retention.

The shape of the extension members may also vary. They may be open-framed and somewhat petal-shaped as shown in FIGS. 2A-2D. In these figures, the extension members 202A, 202B comprise wire segments or ribs that define openings or spaces between the members. However, the invention is not so limited and the extension members may have other shapes. The extension members may, for example, be solid or they may be filled.

In another variation the conduit is constructed to have a delivery state. The delivery state is the configuration of the conduit when it is being delivered through a working channel of a bronchoscope, endoscope, airway or other delivery tool. The maximum outer diameter of the conduit in its delivery state must therefore be such that it may fit within the delivery tool, instrument, or airway.

In one variation, the conduit is radially expandable such that it may be delivered in a smaller working channel of a scope while maximizing the diameter to which the conduit may expand upon deployment. For example, sizing a conduit for insertion into a bronchoscope having a 2 mm or larger working channel may be desirable. Upon deployment, the conduit may be expanded to have an increased internal diameter (e.g., 3 mm.) However, the invention is not limited to such dimensions. It is contemplated that the conduits 200 may have center sections that are expanded into a larger profile from a reduced profile, or, the center sections may be restrained in a reduced profile, and upon release of the restraint, return to an expanded profile.

Additionally, the conduit need not have a smaller delivery state. In variations where the center section is not able to assume a second smaller delivery profile, a maximum diameter of the first or deployed profile will be sufficiently small such that the conduit may be placed and advanced within an airway or a working channel of a bronchoscope or endoscope. Also, in cases where the conduit is self-expanding, the deployed shape may be identical to the shape of the conduit when the conduit is at rest or when it is completely unrestrained.

Additionally the conduit may be partially expanded in its proximal region in the delivery state, as shown in FIG. X. The partially expanded portion would still me sized small enough to fit within the working channel of the bronchoscope, but would be significantly larger (e.g., 0.5-2 mm) larger that the distal portion of the conduit. This partial expansion allows for easy placement of the conduit by providing a physical stop for the conduit within the airway wall. After the conduit is placed the entire conduit can be expanded to its intended expanded shape.

The partial expansion state can also be achieved by partially inflating the proximal section of the conduit with a separate balloon on the delivery device. Another possible method is to design the conduit to preferentially expand the proximal section before the distal section, thereby partially expanding the conduit to create the size differential, placing the stent inside the airway wall with the aid of the stop, and then fully expanding the conduit.

Control Members

The conduit 200 shown in FIGS. 2A-2D also includes diametric-control segments, tethers, or leashes 235 to control and limit the expansion of the center section 208 when deployed. This center-control segment 235 typically is shaped such that when the conduit radially expands, the center-control segment bends until it is substantially straight or no longer slack. Such a center-control segment 235 may be circular or annular shaped. However, its shape may vary widely and it may have, for example, an arcuate, semi-circular, V, or other type of shape which limits the expansion of the conduit.

Typically, one end of the center-control segment is attached or joined to the center section at one location (e.g., a first rib) and the other end of the center-control segment is connected to the center section at a second location (e.g., a rib adjacent or opposite to the first rib). However, the center-control segments may have other constructs. For example, the center-control segments may connect adjacent or non-adjacent center section members. Further, each center-control segment may connect one or more ribs together. The center-control segments may further be doubled up or reinforced with ancillary control segments to provide added control over the expansion of the center section. The ancillary control segments may be different or identical to the primary control segments.

FIG. 2B illustrates the conduit 200 in its deployed configuration. As discussed above, the center-control segments 235 may bend or otherwise deform until they maximize their length (i.e., become substantially straight) such as the center-control segments 235 shown in FIG. 2B. However, as discussed above, the invention is not so limited and other types of center-control segments may be employed.

Figure 2E:
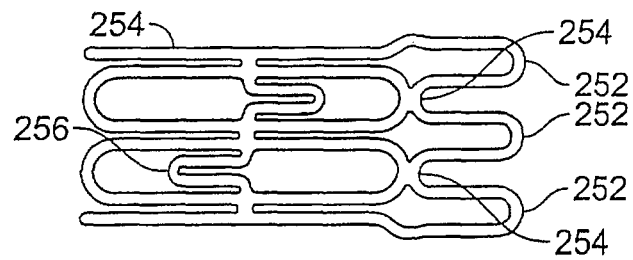
FIG. 2E illustrates a side view of another variation of a conduit in an undeployed shape.
Figure 2F:
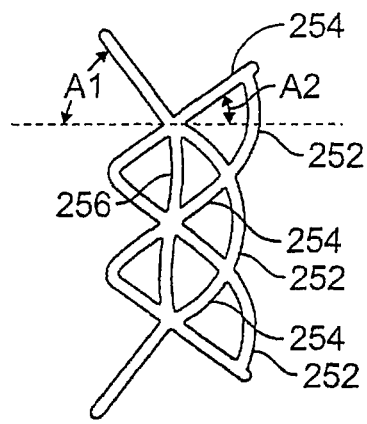
FIG. 2F illustrates a side view of the conduit of FIG. 2E in a deployed state.
Figure 2G:
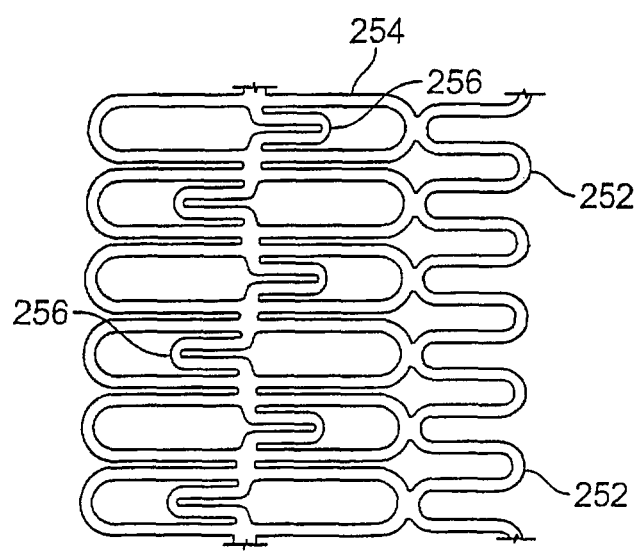
FIG. 2G is a cylindrical projection of the undeployed conduit shown in FIG. 2E.

As shown in FIGS. 2E-2G, control segments 252 may also be used to join and limit the expansion of the extension members 254 or the control segments may be placed elsewhere on the conduit to limit movement of certain features to a maximum dimension. By controlling the length of the control segments, the shape of the deployed conduit may be controlled. In the conduit shown in FIGS. 2E-2G, the conduit includes both center-control segments 256 and distal control segments 252. The center-control segments are arcuate shaped and join adjacent rib sections of the center section and the distal-control segments are arcuate and join adjacent distal extension members.

FIG. 2F illustrates the conduit in a deployed configuration and shows the various control members straightening as the extension members and center section deploy. The proximal extension members, however, are not restricted by a control member and consequently may be deflected to a greater degree than the distal extension members. Accordingly, a conduit having control members connecting, for example, regions of the center section and having additional control segments connecting extension members, may precisely limit the maximum profile of a conduit when it is deployed. This is desirable where overexpansion of the conduit is hazardous.

This also serves to control the deployed shape of the conduit by, for instance, forcing angle A1 to differ from angle A2. Using control segments in this manner can provide for cone-shaped conduits if the various types of control-segments have different lengths. For example, providing longer proximal-control segments than distal-control segments can make angle A1 larger than angle A2. Additionally, cylindrical-shaped conduits may be provided if the center-control segments and the extension-control segments are sized similarly such that angle A1 equals angle A2. Again, the control segments straighten as the conduit expands and the conduit is thus prevented from expanding past a predetermined amount.

The control segments, as with other components of the conduit, may be added or mounted to the center section or alternatively, they may be integral with the center section. That is, the control segments may be part of the conduit rather than separately joined to the conduit with adhesives or welding, for example. The control segments may also be mounted exteriorly or interiorly to the members to be linked. Additionally, sections of the conduit may be removed to allow areas of the conduit to deform more readily. These weakened areas provide another approach to control the final shape of the deployed conduit. Details for creating and utilizing weakened sections to control the final shape of the deployed conduit may be found in U.S. patent Ser. No. 09/947,144 filed on Sep. 4, 2001.

Manufacture and Materials

The conduit described herein may be manufactured by a variety of manufacturing processes including but not limited to laser cutting, chemical etching, punching, stamping, etc. For example, the conduit may be formed from a tube that is slit to form extension members and a center section between the members. One variation of the conduit may be constructed from a metal tube, such as stainless steel, 316L stainless steel, titanium, titanium alloy, nitinol, MP35N (a nickel-cobalt-chromium-molybdenum alloy), etc. Also, the conduit may be formed from a rigid or elastomeric material that is formable into the configurations described herein. Also, the conduit may be formed from a cylinder with the passageway being formed through the conduit. The conduit may also be formed from a sheet of material in which a specific pattern is cut. The cut sheet may then be rolled and formed into a tube. The materials used for the conduit can be those described above as well as a polymeric material, a biostable or implantable material, a material with rigid properties, a material with elastomeric properties, or a combination thereof. If the conduit is a polymeric elastic tube (e.g. a thermoplastic elastomer), the conduit may be extruded and cut to size, injection molded, or otherwise formed.

Additionally, the conduits described herein may be comprised of a shape memory alloy, a super-elastic alloy (e.g., a NiTi alloy), a shape memory polymer, or a shape memory composite material. The conduit may be constructed to have a natural self-assuming deployed configuration, but is restrained in a pre-deployed configuration. As such, removal of the restraints (e.g., a sheath) causes the conduit to assume the deployed configuration. A conduit of this type could be, but is not limited to being, comprised from an elastic polymeric material, or shape memory material such as a shape memory alloy. It is also contemplated that the conduit could comprise a shape memory alloy such that, upon reaching a particular temperature (e.g., 98.5° F.), it assumes a deployed configuration.

Also, the conduit described herein may be formed of a plastically deformable material such that the conduit is expanded and plastically deforms into a deployed configuration. The conduit may be expanded into its expanded state by a variety of devices such as, for example, a balloon catheter.

The conduit's surface may be modified to affect tissue growth or adhesion. For example, an implant may comprise a smooth surface finish in the range of 0.1 micrometer to 0.01 micrometer. Such a finish may serve to prevent the conduit from being ejected or occluded by tissue overgrowth. On the other hand, the surface may be roughened or porous. The conduit may also comprise various coatings and tissue barriers as discussed below.

Tissue Barrier

Figure 3A:
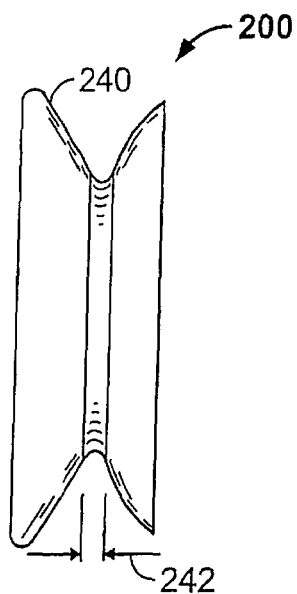
FIG. 3A illustrates a side view of a conduit having a tissue barrier in a deployed state.

FIG. 3A illustrates another variation of a conduit 200 having a tissue barrier 240. The tissue barrier 240 prevents tissue ingrowth from occluding the collateral channel or passage of the conduit 200. The tissue barrier 240 may coaxially cover the center section from one end to the other or it may only cover one or more regions of the conduit 200. The tissue barrier may completely or partially cover the conduit so long as the ends are at least partially open. Moreover, the tissue barrier may only be placed on the center section of the conduit. The tissue barrier 240 may be located about an exterior of the conduit's surface, about an interior of the conduit's surface, or the tissue barrier 240 may be located within openings in the wall of the conduit's surface. Furthermore, in some variations of the invention, the center section 208 itself may provide an effective barrier to tissue ingrowth. The tissue barrier, of course, should not cover or block the entrance and exit of the passageway such that air is prevented from passing through the conduit's passageway. However, in some constructs, the tissue barrier may partially block the entrance or exit of the passageway so long as air may continue to pass through the conduit's passageway.

The tissue barrier may be formed from a material, mesh, sleeve, or coating that is a polymer or an elastomer such as, for example, silicone, fluorosilicone, polyurethane, PET, PTFE, or expanded PTFE. Other biocompatible materials will work, such as a thin foil of metal, etc. The coatings may be applied, for example, by either dip coating, molding, spin-coating, transfer molding or liquid injection molding. Alternatively, the tissue barrier may be a tube of a material and the tube is placed either over and/or within the conduit. The tissue barrier may then be bonded, crimped, heated, melted, shrink fitted or fused to the conduit. The tissue barrier may also be tied to the conduit with a filament of, for example, a suture material.

Still other techniques for attaching the tissue barrier include: solvent swelling applications and extrusion processes; wrapping a sheet of material about the conduit, or placing a tube of the material about the conduit and securing the tube to the conduit. The tissue barrier may be secured on the interior of the conduit by positioning a sheet or tube of material on the inside of the center section and securing the material therein.

The tissue barrier may also be formed of a fine mesh with a porosity or treatment such that tissue may not penetrate the pores. For example, a ChronoFlex™ DACRON® or TEFLON® mesh having a pore size of 100-300 microns may be saturated with collagen or another biocompatible substance. This construct may form a suitable tissue barrier. The mesh may be coaxially attached to a frame such as the open frame structures disclosed above. Still other suitable frames include a continuous spiral metallic or polymeric element. Given the mesh's radial strength or lack thereof, the use of a reinforcement element serves to prevent the implant from collapsing. Also, as described below, other substances may be applied to the exterior surface of the conduit to control elution of various medicines.

Figure 3B:
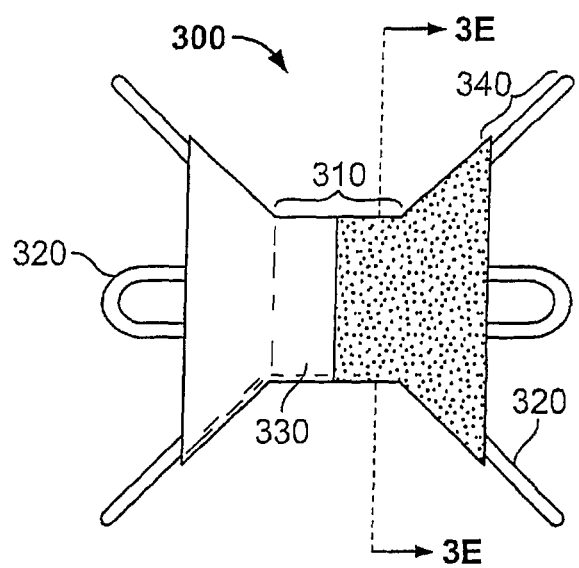
FIG. 3B illustrates a side view of a conduit having a tissue barrier.
Figure 3C:
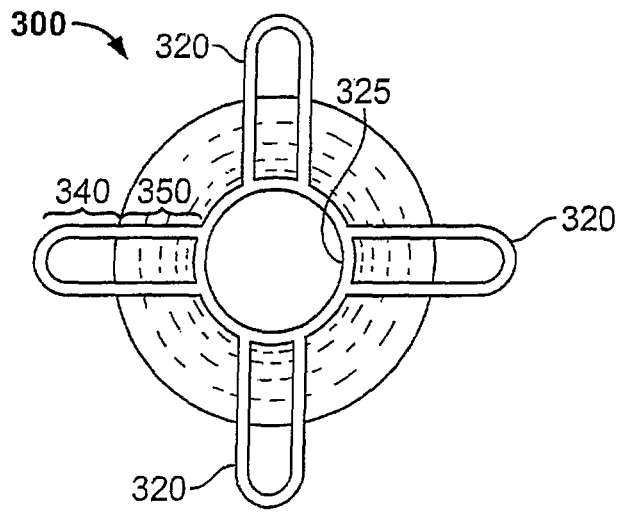
FIG. 3C is a front view of the conduit shown in FIG. 3B.

FIGS. 3B and 3C respectively illustrate a side view and a front view of another conduit 300 having a partial tissue barrier coating. The conduit 300 includes a center section 310, a plurality of extension members 320, and a partial tissue barrier 330. The conduit 300 is thus different than that shown in FIG. 3A in that the center section is longer and that the tissue barrier 330 only partially covers the extension members 320. In particular, the center section 310 shown in FIGS. 3B-3C is cylindrical or tubular-shaped. This shape may be advantageous when a relatively long passageway is desired. Also, it is to be understood that the overall (or three dimensional) shape of the center section, when deployed, is not limited to the shape shown here. Rather, it may have various shapes such as, for example, rectangular, tubular, conical, hour-glass, hemi-toroidal, etc.

Additionally, the tissue barrier 330 covers only a first region 350 of the extension members and leaves a second region 340 of the extension members uncovered. The second or free region 340 of the extension members 320 is shown as being open-framed. However, the invention is not so limited. The second region of the extension members may be solid and it may include indentations, grooves, and recesses for tissue ingrowth. Also, the extension members may include small holes for tissue ingrowth. For example, the second region of the extension members may have a dense array of small holes. In any event, the conduits described herein may include at least one region or surface which is susceptible to tissue ingrowth or is otherwise adherent to the tissue. Accordingly, tissue ingrowth at the second region 340 of the extension members is facilitated while tissue growth into the passageway 325 is thwarted.

Figure 3D:
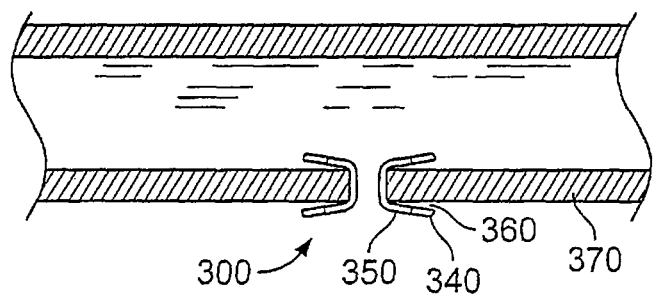
FIG. 3D illustrates a conduit positioned in a channel created in a tissue wall.

As shown in FIG. 3D, tissue growth 360 into the uncovered region 340 further secures the extension members to the tissue wall 370. Free region 340 of the extension members may also include tissue growth substances such as epithelial growth factors or agents to encourage tissue ingrowth. Accordingly, conduit 300 may be configured to engage the tissue wall 370 as well as to allow tissue to grow into predetermined regions of the conduit.

Figure 3E:
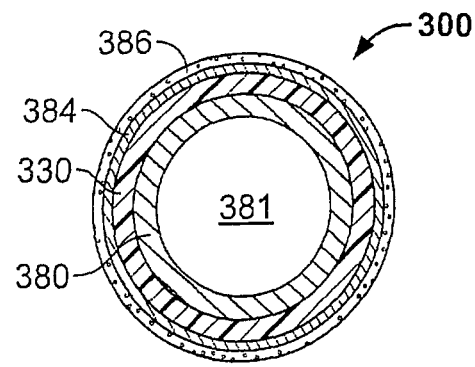
FIG. 3E is a cross sectional view of the conduit shown in FIG. 3B taken along line 3E-3E.

A cross section of a conduit 300 having a bioactive modified surface is shown in FIG. 3E. In particular, the conduit 300 comprises an inner frame layer or ribs 380 which define a passageway 381 for air to flow through. Coaxially surrounding the frame 380 is a tissue barrier 330. Additionally a visualization coating 384 is disposed on the tissue barrier 330. The visualization coating 384 is deposited as described above. A bioactive substance 386 is deposited on the visualization layer either directly or via a binding layer as described below. In this manner, the bioactive substance is disposed on an exterior surface of the conduit and contacts tissue or elutes into the tissue when the device is deployed in a channel. However, it is contemplated that additional layers may be added such as, for example, an additional silicone or bioabsorbable layer over (or in combination with) the visualization layer.

Also the order of the layers may be different than that described above. For example, the visualization layer may be disposed over the bioactive layer. Also, not all coatings and materials shown in FIG. 3E are necessary to carry out the present invention. For instance, the bioactive substances in some cases may be deposited directly on the open-frame 380.

The bioactive layer may also serve as the visualization coating or tissue barrier in some instances. For example, silicone and one or more bioactive substances may be mixed together and disposed on the conduit as a single coating. The single integral layer (or matrix) may serve both to physically and chemically prevent tissue from filling the conduit's passageway. It may also be visually apparent during a procedure.

The bioactive compounds may be combined, impregnated, absorbed or attached to any of the implants described herein. For example, a bioactive substance may be impregnated into a polymeric conduit or a metal conduit having a polymeric coating. These polymer systems hold the drug, allowing it to gradually elute or slowly leach from the polymer body or coating. Useful polymer systems include a polymer that is biocompatible and minimizes irritation to the tissue wall when the conduit is implanted. The polymer may be either a biostable or a bioabsorbable polymer depending on the desired rate of release or the desired degree of polymer stability, but a bioabsorbable polymer, unlike a biostable polymer, will not be present long after implantation to cause any adverse, chronic local response Examples of bioabsorbable polymers include but are not limited to poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly (glycolic acid-co-trimethylene carbonate), polyphosphoester, polyphosphoester urethane, poly(amino acids), cyanoacrylates, poly(trimethylene carbonate), poly (iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, fluorosilicones, and polyesters could be used. Also, hydrogels may be used to carry the drug.

Examples of other types of polymers that may be useful include hut are not limited to polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; rayon triacetate; cellulose, cellulose acetate, cellulose butyrate; cellulose acetate butyrate; cellophane; cellulose nitrate; cellulose propionate; cellulose ethers; and carboxymethyl cellulose, It may be possible to dissolve and cure for polymerize) these polymers on the conduit so that they do not leach into the tissue and cause any adverse effects on the tissue, The conduits may be coated or impregnated variously. For example, a polymer solution may be applied to the conduit and the solvent allowed to evaporate, thereby leaving on the conduit surface a coating of the polymer and the therapeutic substance. Typically, the solution can be applied to the conduit by either spraying the solution onto the conduit or immersing the conduit in the solution. In either a coating applied by spraying or by immersion, multiple application steps are generally desirable to provide improved coating uniformity and improved control over the amount of therapeutic substance to be applied to the conduit.

The bioactive substances may be deposited on the exterior surface of the conduit evenly or in discrete (intermittent) amounts. The thickness of the coatings may be uniform or the thickness may vary across certain regions of the conduit. This may provide higher therapeutic doses corresponding to certain regions of the injury site. For example, it may be desirable to provide a higher concentration of a bioactive substance near the ends of the conduit rather than in the center section.

The bioactive coatings may be selectively applied by spraying the bioactive substance onto uncovered regions of the conduit. For example, the bioactive substances may be disposed on at least a portion of the tissue barrier, the open-frame, or mesh structure. The substances may also be applied by dipping, painting, printing, and any other method for impregnating or depositing a substance onto the conduit surface.

Figure 3F:
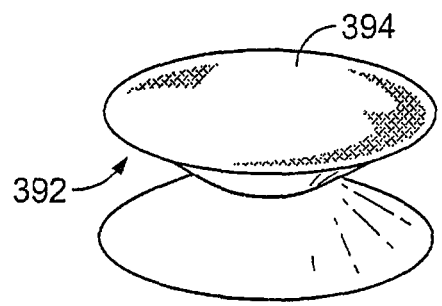
FIGS. 3F-3G depict another conduit including a membrane that supports a bioactive substance; the bioactive substance may be coated on the membrane.
Figure 3G:
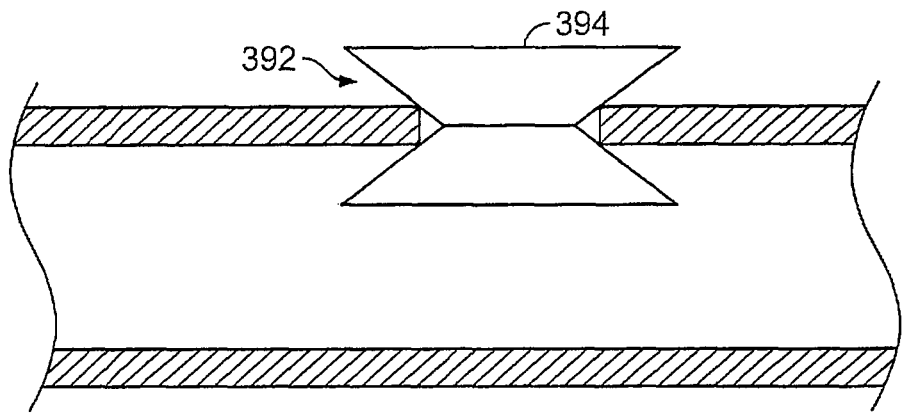

FIGS. 3F-3G depict another conduit 392 that supports a bioactive substance. In particular, conduit 392 includes a membrane, mesh, or framework 394 that covers one or both ends of the conduit. A bioactive substance is associated with the mesh. For example, a bioactive substance may coat the mesh. FIG. 3G shows the conduit deployed in an airway and the mesh 394 is facing the parenchyma. The coated mesh may be present on one end or both ends of the conduit. Also, a wide variety of bioactive substances may be applied to the mesh and the conduit. Antiproliferative or cytotoxic substances, for example, may be applied to any portion of the mesh, the inside of the conduit, the outside of the conduit, or both the inside and outside of the conduit.

Binding or tie layer materials may be applied to the exterior surface of the conduit upon which the bioactive agents are deposited. Cross-linked polymers and or biodegradable polymers such as, for example, chondroitin sulfate, collagen and gelatin may be applied to the exterior surface of the conduit prior to depositing other substances.

Solvent-type coatings, gels or mediums may also be used in combination with a conduit body. The advantage of a solvent system stems from the unique characteristics of the airway. Amongst other things, the airway is specialized to transport air and mucus. In an airway, as opposed to a blood vessel, diffusion of a drug to a target site may be slow since there is not a natural flowing liquid (such as blood in a blood vessel) to dissolve the polymer and disperse the drug into the tissue. For this reason, a paste, viscous solvent, or gel may desirably be disposed on the exterior of the conduit to facilitate the diffusion of drugs into nearby tissue.

Thin coatings may also be deposited on the conduit surfaces. Thin coatings of, for example, tantalum may be applied to the conduits to increase the radiopacity, to change the charge on the surface of the conduit, to provide a tie layer upon which other agents may be deposited, or for other reasons. Physical vapor deposition such as plasma deposition, vapor phase deposition, ion plating and ion implantation may be useful to apply such a layer to the conduit frame or mesh structure.

Visualization Feature

The conduit shown in FIG. 3A also includes a visualization ring or marker 242. The marker 242 is visually apparent during a procedure. The marker is observed as the conduit is placed in a collateral channel and, when the marker is even with the opening of the channel, the conduit may be deployed. In this manner, the visualization feature facilitates alignment and deployment of the conduits into collateral channels.

The visualization ring or mark may be a biocompatible polymer and have a color such as white. Also, the visualization feature may protrude from the center section or it may be an indentation(s). The visualization mark may also be a ring, groove or any other physical feature on the conduit. Moreover, the visualization feature may be continuous or comprise discrete segments (e.g., dots or line segments).

The visualization feature may be made using a number of techniques. In one example, the mark is a ring formed of silicone and is white. The polymeric ring may be spun onto the tissue barrier. For example, a clear silicone barrier may be coated onto the conduit such that it coaxially covers the extension members and the center section as shown in FIG. 3A. Next, a thin ring of white material such as a metal oxide suspended in clear silicone may be spun onto the silicone coating. Finally, another coating of clear silicone may be applied to coat the white layer. The conduit thus may include upwards of 1-3 layers including a tissue barrier, a visualization mark layer, and a clear outer covering.

The shape of the visualization mark is not limited to a thin ring. The visualization mark may be large, for example, and cover an entire half of the conduit as shown in FIG. 3B. The visualization mark may, for example, be a white coating disposed on the proximal or distal half of the conduit. The visualization mark thus may extend from an end of the extension members to the center section of the conduit. As explained in more detail below, when such a device is deposited into a channel created in lung tissue, the physician may observe when one-half of the conduit extends into the channel. This allows the physician to properly actuate or deploy the conduit to secure the conduit in the tissue wall.

Accordingly, the visualization member is made visually apparent for use with, for example, an endoscope. The visualization feature, however, may also be made of other vision-enhancing materials such as radio-opaque metals used in x-ray detection. It is also contemplated that other elements of the conduit can include visualization features such as but not limited to the extension members, tissue barrier, control segments, etc.

In some variations of the invention, it was found that incorporation of a bioactive, as discussed herein, or other substance into the coating caused a coloration effect in the composition layer (e.g., the polymer turns white). This coloration obscures the support member structure in the layer making it difficult to identify the edges and center of the support member or implant. As discussed herein, placement of the implant may depend upon positioning the center of the implant within the opening in tissue. If the support member structure is identifiable, then one is able to visually identify the center of the implant. When the composition colors obscures the support member or renders the implant otherwise opaque, it may become difficult to properly place the device. This may be especially true when the composition layer extends continuously over the support member.

Additionally, the coloration may render the visualization mark difficult to identify especially under direct visualization (e.g., using a scope) In some cases it was undesirable to simply add additional substances on or in the composition layer for marking because such substances could possibly interfere with the implant's ability to deliver the substance as desired. To address these issues, a variation of the invention includes a delivery device for delivering an expandable implant (such as those described herein and in the cases referenced herein), where the delivery device includes an expandable member having an expandable implant located about the expandable member. Where the implant and the expandable member are of different visually identifiable colors or shades such that they distinction is easy to identify under endoscopic or bronchoscopic viewing.

In one example, a balloon catheter has a colored sleeve located about the balloon. The sleeve comprises a visually identifiable color where selection of the colors should ease identification of the implant an endoscopic visualization system (e.g., blue or a similar color that is not naturally occurring within the body.) The implant is placed about the sleeve where the proximal and distal areas of the implant would be identifiable by the difference in color. Such a system allows a medical practitioner to place the implant 200 properly by using the boundary of the implant 200 to guide placement in the tissue wall. The sleeve may be fashioned from any expandable material, such as a polymer. Optionally, the sleeve may also provide an elastic force to return the balloon to a reduced profile after expansion of the balloon. Such a system allows for identification without affecting the properties of the implant.

It should be noted that variations of the invention include coloring the balloon itself, or other expandable member, a color that meets the above criteria.

In another variation, the visualization mark may comprise providing a contrast between the implant and a delivery catheter. In one example the implant is appears mostly white and while mounted on a contrasting color inflation balloon. In this example the implant would be placed over a blue deflated balloon catheter. The proximal and distal areas of the implant would be flanked by the deflated blue balloon, thus giving the appearance of a distinct distal and proximal end of the implant. This would allow a physician to place the implant properly by using the blue flanks as a guide for placing the central white portion in the tissue wall. Similarly, a colored flexible sheath covering the balloon would also suffice.

It is noted that while the visualization features described above are suitable for use with the implants described herein, the inventive features are not limited as such. The features may be incorporated into any system where placement of an implant under direct visualization requires clear identification of the implant regardless of whether the implant is opaque or colored.

Bioactive Agents

As discussed above, the bio-active substance or combination of bioactive substances is selected to assists in modifying the healing response as a result of the trauma to the lung tissue resulting from creation of the collateral channel. As noted above, the term lung tissue is intended to include the tissue lining the airway, the tissue beneath the lining, and the tissue within the lung but exterior to the airway (e.g., lung parenchyma.) The purpose of modifying the healing response is to further extend the patency of the channel or implant to increase the duration which trapped gasses may exit through the implant into the airways. The term antiproliferative agent is intended to include those bioactive substances that directly modify the healing response described herein.

The bioactive substances are intended to interact with the tissue of the surgically created channels and in particular, lung tissue. These substances may interact with the tissue in a number of ways. They may, for example, 1.) accelerate cell proliferation or wound healing to epithelialize or scar the walls of the surgically-created channel to maintain its patent shape or 2.) the substances may inhibit or halt tissue growth when a channel is surgically created through an airway wall such that occlusion of the channel due to tissue overgrowth is prevented. Additionally, other bioactive agents may inhibit wound healing such that the injury site (e.g., the channel or opening) does not heal leaving the injury site open and/or inhibit infection (e.g., reduce bacteria) such that excessive wound healing does not occur which may lead to excessive tissue growth at the channel thereby blocking the passageway. By creating an extra-anatomic passage and inhibiting wound healing as discussed above it is possible to create and maintain the extra-anatomic opening in an airway wall at a target site such that patency of the extra-anatomic opening is artificially extended beyond an otherwise natural healing response.

A variety of bioactive substances may be used alone or in combination with the devices described herein. Examples of bioactive substances include, but are not limited to, antimetabolites, antithrobotics, anticoagulants, antiplatelet agents, thorombolytics, antiproliferatives, antinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium, epithelium) and tissue formation (neointimal tissue).

Still other bioactive agents include but are not limited to analgesics, anticonvulsives, anti-infectives (e.g., antibiotics, antimicrobials), antineoplastics, H2 antagonists (Histamine 2 antagonists), steroids, non-steroidal anti-inflammatories, hormones, immunomodulators, mast cell stabilizers, nucleoside analogues, respiratory agents, antihypertensives, antihistamines, ACE inhibitors, cell growth factors, nerve growth factors, anti-angiogenic agents or angiogenesis inhibitors (e.g., endostatins or angiostatins), tissue irritants (e.g., a compound comprising talc), poisons (e.g., arsenic), cytotoxic agents (e.g., a compound that can cause cell death), various metals (silver, aluminum, zinc, platinum, arsenic, etc.), epithelial growth factors or a combination of any of the agents disclosed herein.

Examples of agents include pyrolitic carbon, titanium-nitride-oxide, taxanes, fibrinogen, collagen, thrombin, phosphorylcholine, heparin, rapamycin, radioactive 188Re and 32P, silver nitrate, dactinomycin, sirolimus, everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, 7-epi-taxol, cephalomannine, baccatin III, baccatin V, 10-deacetylbaccatin III, 7-epi-10-deacetylbaccatin III,docetaxel.

Of course, bioactive materials having other functions can also be successfully delivered in accordance with the present invention. For example, an antiproliferative agent such as methotrexate will inhibit over-proliferation of smooth muscle cells and thus inhibit restenosis. The antiproliferative is desirably supplied for this purpose until the tissue has properly healed. Additionally, localized delivery of an antiproliferative agent is also useful for the treatment of a variety of malignant conditions characterized by highly vascular growth. In such cases, an implant such as a implant could be placed in the surgically created channel to provide a means of delivering a relatively high dose of the antiproliferative agent directly to the target area. A vasodilator such as a calcium channel blocker or a nitrate may also be delivered to the target site. The agent may further be a curative, a pre-operative debulker reducing the size of the growth, or a palliative which eases the symptoms of the disease. For example, tamoxifen citrate, Taxol® or derivatives thereof Proscar®, Hytrin®, or Eulexin® may be applied to the target site as described herein.

Variations of the invention may also include fibrinolytics such as tPA, streptokinase, or urokinase, etc. Such fibrinolytics prevent or reduce the accumulation of fibrin within the opening. Accumulation of fibrin in the opening may result from inflammation of the tissue. The fibrin may form a structure which makes it easier for tissue to grow into the opening using the fibrin structure as a framework. Use of fibrinolytics, either topically, locally, or on the implant, serves to remove or hinder the network of fibrin from forming within the opening (or implant) and therefore aids in modifying the healing response.

In the event that poisonous and toxic compounds are delivered, they should be controlled so that inadvertent death of tissue does not occur. The poisonous agent should be delivered locally or only be effective locally. One method for delivering the bioactive agent locally is to associate the bioactive agent with an implant. For example, the implants described herein may include a bioactive substance or medicine deposited onto the interior, the exterior, or both the interior and exterior surfaces of the implant. The bioactive substance may remain on the implant so that it does not leach. Cells that grow into the surgically created channel contact the poison and die. Alternatively, the bioactive agent may be configured to gradually elute as discussed below.

When used in the lungs, the implant modifies the healing response of the lung tissue (e.g., at the site of newly created hole/channel) for a sufficient time until the healing response of the lung tissue subsides or reduces such that the hole/channel becomes a persistent air path. For example, the implant and bioactive substance will modify the healing response for a sufficient time until the healing response is reduced and, from a visual observation, the body treats the opening essentially as a natural airway passage rather than as an injury to the airway wall.

In one variation of the invention which modifies the healing response as describe above, the implant provides a steady release rate of bio-active substance as well as has a sufficient amount of available bio-active substance to modify the healing response of the lung tissue. As noted herein, the term lung tissue is intended to include the tissue lining the airway, the tissue beneath the lining, and the tissue within the lung but exterior to the airway (e.g., lung parenchyma.) Such a delivery profile allows for a concentration gradient of drug to build in these tissues adjacent to the delivery site of the implant.

It is believed that forming the concentration gradient affects the healing response of the lung tissue so that the implant does not become occluded as a result of the healing response. Because the implant is often placed in the airway wall it is exposed to the healing process of the multiple tissues. Providing a sufficient amount of bio-active substance allows for the formation of a concentration of the bio-active substance across these various tissues. In one variation of the invention it is believed that the fluids from these tissues enter into the composition layer of the device. The fluids then combine with the bio-active substances and migrate out of the composition layer to settle into the lung tissue. A concentration gradient forms when the drug 'saturates' local tissue and migrates beyond the saturated tissues. Furthermore, by providing a sufficient delivery rate, the healing response may be affected or suppressed during the critical time immediately after the wounding caused by creation of the collateral channel when the healing response is greatest.

To select a proper combination of drug and polymer, it is believed that the solubility parameter of the polymer must be matched with the bio-active substance to provide an acceptable slow elution rate from the polymer. Next, the polymer itself must be selected to have the proper attributes, such as a proper diffusion coefficient (to slow fluid entering and departing from the implant), and proper mechanical expansion properties (to allow for the significant expansion of the polymer to accommodate formation of the grommet shape.)

The solubility parameter is defined as the square root of the cohesive energy of the molecules in a compound. The level of control that a polymer has over the elution of a drug is the difference between the solubility parameters of the polymer and the solubility parameter of the drug. To select a polymer with the approximate diffusion a polymer with a high internal density could be selected to be less permeable to a complex molecule such as paclitaxel. Using a polymer with high internal density also accommodated the significant expansion required of the polymer to form the structure necessary to grommet about the airway wall. An example of the polymer selection is found below.

It is also important to note that paclitaxel is a taxane that is regarded as a microtubule stabilizer. The benefits of a microtubule stabilizing substance for use in vascular drug eluting stents is discussed, for example, in U.S. Pat. No. 5,616,608 to Kinsella et al. This type of drug operates to enhance microtubule polymerization which inhibits cell replication by stabilizing microtubules in spindles which block cell division. In contrast to the vascular applications, the implant for use in the present invention may use microtubule stabilizing substances such as taxanes (e.g., paclitaxel) as well as those microtubule destabilizing substances that are believed to promote microtubule disassembly in preventing cell replication. Such destabilizing substances include, but are not limited to vincristine, vinblastine, podophylotoxin, estramustine, noscapine, griseofulvin, dicoumarol, a vinca alkaloid, and a combination thereof.

Additionally, the exterior surface of the implant may be treated via etching processes or with electrical charge to encourage binding of the bioactive substances to the implant. The exterior surface may also be roughened to enhance binding of the medicine to the surface as discussed in U.S. Patent Application Publication No. 2002/0098278. See also U.S. Patent Application Publication Nos. 2002/0071902, 2002/0127327 and U.S. Pat. No. 5,824,048 which discuss various techniques for coating medical implants.

Although the implant may comprise a frame or body with a bioactive matrix disposed or otherwise associated therewith, the invention is not so limited. In one variation, the support member is formed from a polymer and the composition is joined to the polymeric support member. Alternatively, the bioactive substances may be placed directly onto the polymeric support member.

Various additional substances may be used incorporated into the device to reduce an adverse reaction resulting from possible contact with the implant and the airway wall. Adverse reactions include, but are not limited to, granulation, swelling, and mucus overproduction. These substance may may also be inhaled, injected, orally applied, topically applied, or carried by the implant. These substances may include anti-inflammatory, infection-fighting substances, steroids, mucalytics, enzymes, and wound healing-accelerating substances. Examples of these substances include but are not limited to, acetylcysteine, albuterol sulfate, ipratropium bromide, dornase alfa, and corticosteroids.

As noted above, conventional vascular drug eluting devices are not designed for exposure multiple tissue environments. Moreover, those devices are placed in an environment where a constant flow of blood creates an environment requiring a different delivery mechanism and rate. As noted herein, experiments with conventional coronary drug eluting implants demonstrated that such devices were unsuitable.

Channel Creation Devices and Methods

Figure 4A:
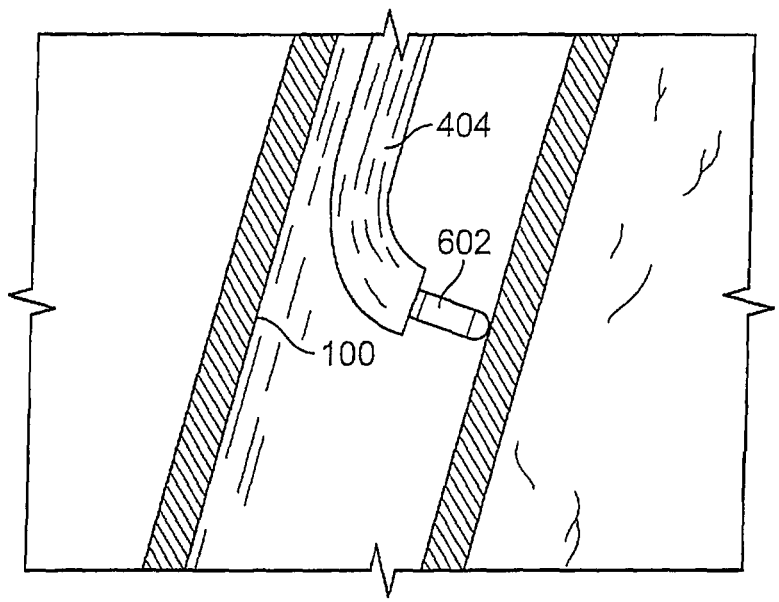
FIGS. 4A-4C a variation of selecting a site, creating a channel at the site using a less traumatic hole-maker, and expanding the channel.
Figure 4B:
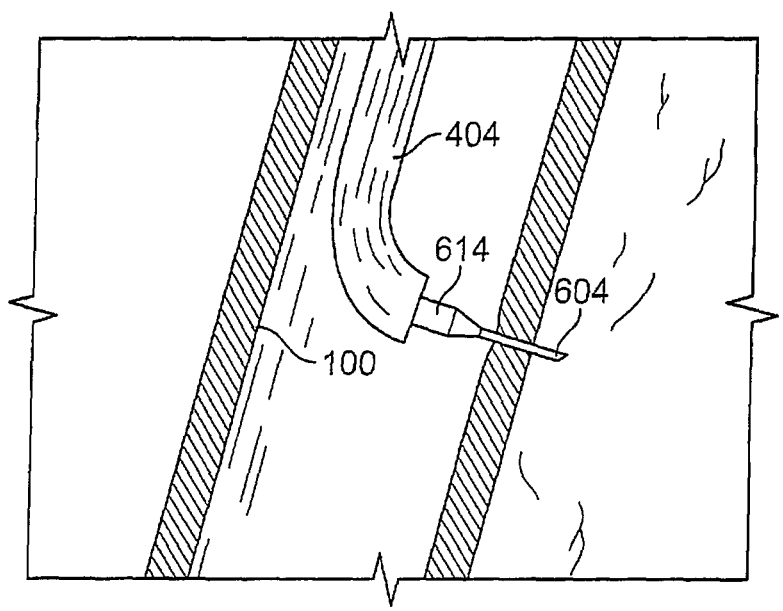
Figure 4C:
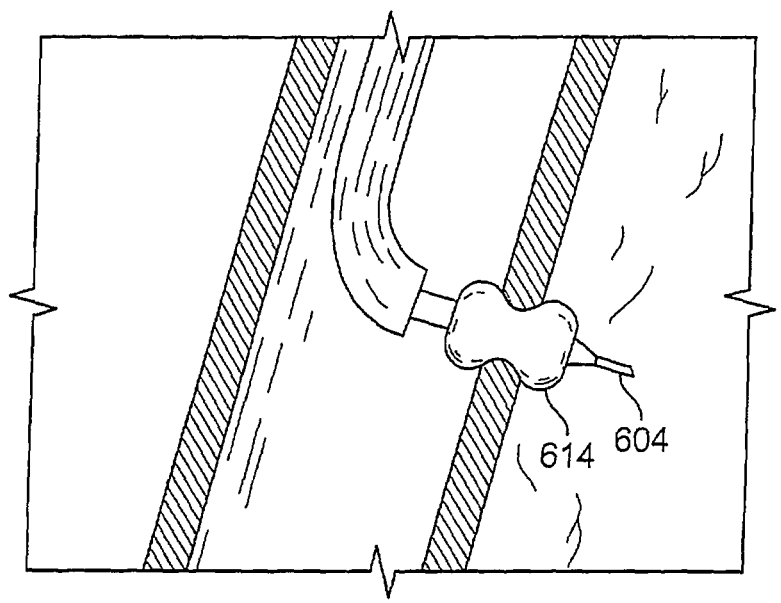

As discussed above, the use of low temperature devices, (e.g., mechanical devices, newer generation RF-type devices, etc.) to create the channel may result in less trauma to surrounding tissue and minimize the healing response of the tissue. FIGS. 4A-4C illustrates creation of the collateral channel and selecting a treatment site in the airway 100. As will be discussed in more detail below, a single device may be used to select the site and create the channel. Moreover, another variation of the invention includes using such a device to deploy the conduit at the target site. However, the invention also contemplates using separate devices to perform each step or a combination of steps.

As shown in FIG. 4A, a device 602 is advanced, for example, via a bronchoscope 404, into the airway 100. The device can be delivered through a natural respiratory opening such as an oral opening and into the airway 100. A potential treatment site is then inspected to determine whether or not a blood vessel is in proximity to the site. Naturally, if a blood vessel is detected, the surgeon has the option of selecting a different site. The device 602 may be a Doppler ultrasound device, a thermal device, an imaging device, etc.

FIG. 4B illustrates another variation of selecting a site for a channel. In this variation, a piercing member (e.g., a blade affixed to a shaft, a needle, cannula, sharpened tube or rod, etc.,) 604 is advanced into the airway wall. Once the piercing member 604 is inserted into the airway wall, the surgeon may inspect the area for blood to determine whether the device punctured a blood vessel. After the opening is created the surgeon may also remove collect a biopsy of material behind the airway wall. If the opening is large enough as created by a balloon, as described herein, the surgeon may use forceps to visually obtain the sample. This may be preferable to a blind method of obtaining biopsies, considering that the risk of bleeding may be reduced because the area has been scanned for blood vessels.

The piercing member 604 may have a lumen and may be open at a distal end or closed. In those cases where the piercing member 604 is hollow and has an opening at or near the distal end, the surgeon may aspirate the site using the piercing member 604 to determine whether a blood vessel is present and/or penetrated. For example, flashback catheters contain chambers which will fill with blood upon the penetration of a vessel by the distal tip of the catheter. The piercing member may be incorporated to have a flashback chamber to detect the presence of blood flow from a penetrated vessel. Using these approaches, a target site may not be selected until after a hole is made in the airway 100 wall. It should be noted that a piercing member may be of a diameter which results in closure of the puncture site upon removal of the piercing member. Alternatively, the piercing member may be of a sufficient size or construction that the hole remains open upon removal of the piercing member. In any case, the piercing member or another device may be used to mark the site of the opening (e.g., via ink, dye, physical marker, via application of electrical energy, etc.) Furthermore, the invention includes use of both a detecting device as described above in combination with a piercing member. For example, the site may be inspected by the detecting device prior to insertion of a piercing member.

The piercing member lumen may also used to deliver therapeutic fluids to the lungs. For example, in case of bleeding after channel creation the physician may apply epinephrine or saline the lungs. Alternatively the physician may use the piercing member to apply epinephrine to the airway wall prior to creation of the channel, to prevent bleeding. This may be done by injecting directly into the airway wall at or about the site of passage creation; singly or in a surrounding pattern of multiple applications. The physician may also use the piercing member lumen to apply any of the bioactive agents discussed herein, before or after passage creation.

Because it may be desirable to reach remote airways within the lung, it may be necessary to fully articulate the scope 404 to access and inspect a desirable site. Therefore, to inspect the site and create an opening, it may be desirable to maintain the scope 404 in a fixed position and simply advance/retract various components of the scope or devices in the scope. Accordingly, a piercing member may be selected to have a length that will sufficiently pass through the airway wall, while being small enough that it will also pass through a fully articulated bronchoscope. Furthermore, the piercing member may have sections of varying stiffness where a distal portion, (that is sufficient stiff to penetrate the tissue) may be of a length such that it is able to advance through a fully articulated bronchoscope. For example, the piercing member may comprised of a sharpened cannula which has a length from between 2 mm to 30 mm. The diameter may range between 16 Ga to 25 Ga or larger. The cannula may be affixed to a catheter having a relatively flexible proximal portion. In any case, the length of the piecing member 604 may vary as needed.

The piercing member is not limited to a cannula, it may be of solid construction, such as a sharpened rod or wire. Additionally the piercing member may be adapted with an elongate member, such as a wire, rod, or tube, which extends throughout the device. The purpose of the elongate member is to provide column strength to the piercing member and necessary bending resistance to the catheter, because it has been found that the device must have high column strength to effectively pierce the airway wall, otherwise the device will deflect and not create a passageway. The elongate member may be utilized to expose and retract the piercing member within the catheter, as the elongate member may extend throughout the device to a user interface. The elongate member and piercing member may also be constructed from one piece of material, thereby making them one part. Alternatively the elongate member may be a separate part welded, bonded, mechanically attached, or a combination thereof, to the piercing member.

However, it is understood, that the current invention is not limited to any particular length of the piercing member. Furthermore, the piercing member may be comprised of a resilient polymer, a polymer with a reinforced structure (e.g., a braid, coil, etc.), a super-elastic alloy, a metallic material with sufficient resilience, etc, such that it may navigate through a fully articulated bronchoscope yet return to its original profile upon exiting the working channel of the scope.

In some variations of the invention, the piercing member of the device may be retractable within a lumen of an elongate shaft so as to prevent damage to the bronchoscope or to tissue as the device advances to the target site. Additionally the piercing member may be retracted after the initial piercing of the airway wall, and blunt trauma may be used to further push the remaining portion of the catheter into the airway wall. This technique may help avoid additional bleeding and pneumothoraxes from an exposed piercing member. The catheter may be advanced to tortuous locations, therefore the device may incorporate low friction materials to make it easier to reach the treatment site. The materials may be selected from a group of low friction polymers, for example PTFE. Low friction materials may also be applied as a coating onto the pierced member or elongate member, for example PTFE or titanium nitride. Reducing the contact surface area between the members may also help to reduce friction. Adding or removing material from the surfaces of members is one way to reduce contact surface area. For example attaching a closed coiled spring around the piercing member or elongate member, effectively reduces the surface area contacted between the elongate member and lumen because only the peaks of the coils contact the lumen.

In additional variations of the invention, as shown in FIG. 4C, a balloon catheter may be configured with a piercing member 604. In this variation the balloon 614 advances into the opening created by the piercing member (in which case the piercing member either retracts into the catheter or advances with the catheter.) The balloon 614 would then deploy to dilate the opening for ease of later inserting a conduit. Alternatively, a conduit may be located on the balloon itself and deployed on inflation of the balloon. Examples of variations of such a balloon catheter may be found below. Furthermore, the needle may be affixed to a tapered introducer type device which is able to dilate the opening.

The piercing member 604 may also be used to deliver bioactive substances (as described herein) to the site of the opening. In such a case, the piercing member 604 may deliver the bioactive substance during creation of the opening (e.g., see FIG. 4B) or after dilation of the opening (see e.g., FIG. 4C). In another variation of the invention, the piercing member 604 may be have a multi-lumen cross-section with different lumens being reserved, for example, for inflating the balloon, aspirating the site for blood, drug delivery, and suction of mucous/fluids at the site. In any of the variations described herein, an obturator (not shown) may be used to fill a lumen during advancement of the piercing member into tissue so that the lumen does not become blocked with tissue or other debris. The obturator may be a guide-wire, polymeric column of material, etc.

Figure 4D:
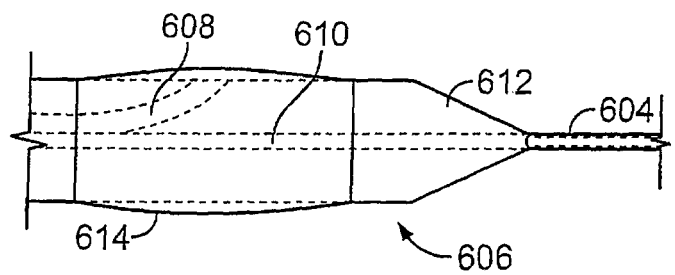
FIGS. 4D-4K illustrate variations of piercing members for creating collateral channels.

FIG. 4D illustrates a variation of a balloon catheter 606 having a piercing member 604. In this variation, the balloon catheter 606 comprises two lumens 608, 610. One lumen 608 is fluidly coupled to the interior of the balloon 614 while the second lumen 610 extends through the piercing member 604. It is understood that the device 606 may be configured to have any number of lumens as required. As discussed above, the piercing member 604 may either be fixedly attached to the distal end of the balloon catheter 606. Alternatively, the piercing member 604 may be retractable into the balloon catheter 606 so that it does not cause damage to lung parenchyma when the catheter 606 is inserted into the airway 100 wall. As illustrated, the balloon catheter 606 may have a tapered section 612 between the piercing member 604 and the balloon 614 to assist in insertion of the balloon 614 into the opening 112.

Figure 4E:
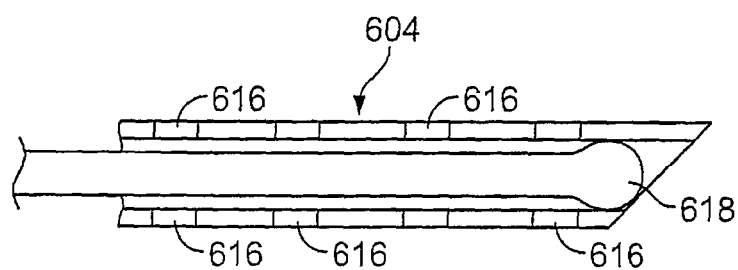

FIG. 4E illustrates an additional variation of a piercing member 604 according the present invention. As illustrated, the piercing member 604 may have a number of ports 616 (e.g., openings, holes, etc.). The ports 616 may allow for either aspiration of blood or delivery of bio-active substances as described herein. Furthermore, although the piercing members 604 shown herein are configured with a beveled tip, it is contemplated that the tip may be any type of tip sufficient to penetrate the airway wall. For instance, the tip may be non-beveled with sharpened edges, the tip may be a trocar tipped needle, or any other available needle tip configuration. The piercing member 604 of FIG. 4E is also shown with an obturator placed therein. In this configuration, the obturator 618 blocks the lumen of the piercing member 604 at the distal end. Moreover, as shown, a portion of the obturator 618 may be sized such that it is smaller than a lumen of the piercing member 604 to allow for delivery of substances or aspiration through the ports 616.

Figure 4F:
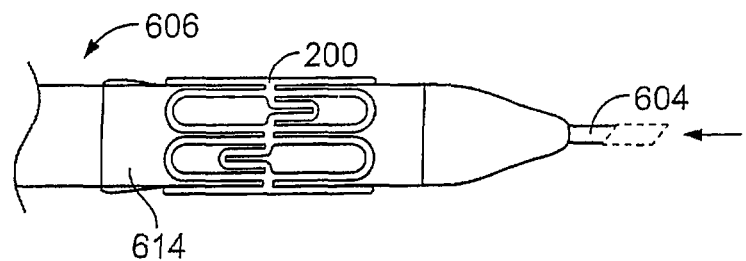

FIG. 4F illustrates yet another variation of a balloon catheter 606 having a piercing member 604. In this variation, as indicated by the arrow, the piercing member 604 is capable of being retracted into the catheter 606. The ability to retract the piercing member 604 into the catheter 606 reduces the possibility of the piercing member 604 causing damage to any lung tissue that is behind the airway wall. Clearly, this variation combines the channel-making step with the conduit deployment step. Also, as shown in the figure, the catheter 606 may have a conduit 200 placed over the balloon 614. Such a variation may create the opening or channel and then deploy the conduit 200 with a single device.

Figure 4G:
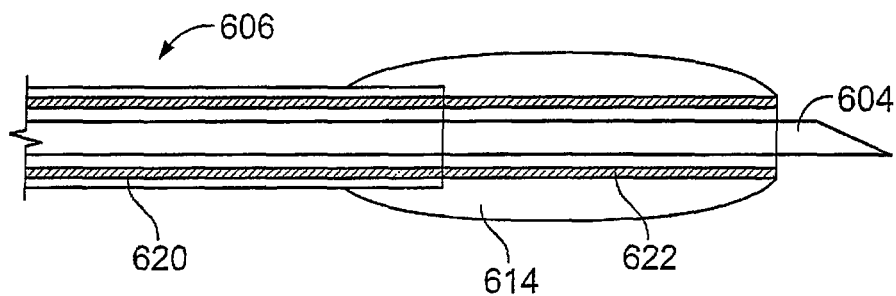

FIG. 4G illustrates another variation of a balloon catheter 606 where the piercing member 604 is slidably located within the catheter 606. In this variation, the catheter 606 contains an outer and inner sheaths 620, 622 which define two lumens. The lumen defined by the inner sheath 622 extends to the distal end of the catheter 606 and may be used to deliver bioactive substances, for suction, or for irrigation.

It is also contemplated that variations of the invention include a piercing member which is affixed to the catheter. Alternatively, the piercing member could have a flexible body that extends through the catheter to a proximal hub which is able to be coupled to a vacuum source, a source of medication, etc. Furthermore, either the piercing member and/or balloon catheter may be "pre-loaded" with a bioactive substance. Such a feature allows improves the precision of amount of substance delivered to the desired site.

Figure 4H:
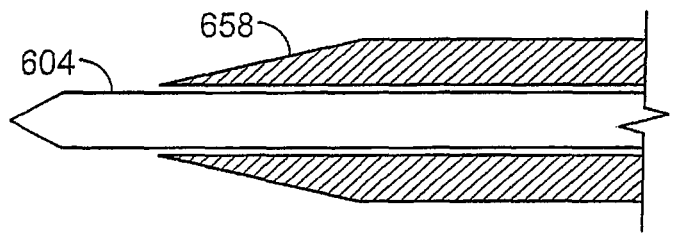

As mentioned above, the piercing member 604 may be of a sufficient size or construction that the hole remains open upon removal of the piercing member. Once variation of this as shown in FIG. 4H, where the device has a conical tip 658 with a lumen extending through out. A piercing member 604 is extendable past the distal tip to pierce the airway wall, after the initial opening is made, the rest of the device can be driven into the airway wall, gradually expanding the hole to a desirable diameter which allows the conduit to be subsequently placed.

The makeup of airway tissue may require a considerable amount of force to create a channel with the piercing device. Therefore, it will generally be easier to create a channel if the device has sufficient column strength to avoid bending of the device when applying a force at the proximal end of the device.

Additional variations of the invention may incorporate a nondistensible balloon to overcome the toughness of the airway tissue. Nondistensible balloons are generally made up of relatively inelastic materials consisting of PET, nylons, polyurethanes, polyolefins, PVC, and other crosslinked polymers. The makeup of airway tissue may be very tough and resist radial expansions. Therefore it will be generally easier to expand the channel in the airway wall using high pressure nondistensible balloons (>6 atm), which generally inflate in a uniform shape.

Nondistensible balloons will occupy a greater mass than distensible balloons because they in an inelastic predetermined form. Too much balloon mass will have too large of a working diameter, which in turn will hinder entry into a channel. Working diameter is the smallest effective diameter opening the uninflated nondistensible balloon can be inserted into. Therefore it is desirable to have the uninflated nondistensible balloon to have a working diameter close to the diameter of the piercing device 604. This can be attained by using a thin walled balloon, using a balloon with a small distal profile, by using a balloon with a distal end which is close in actual diameter to the diameter of the piercing member, or by using a balloon which folds into a low profile state, or a combination of these.

Figure 4I:
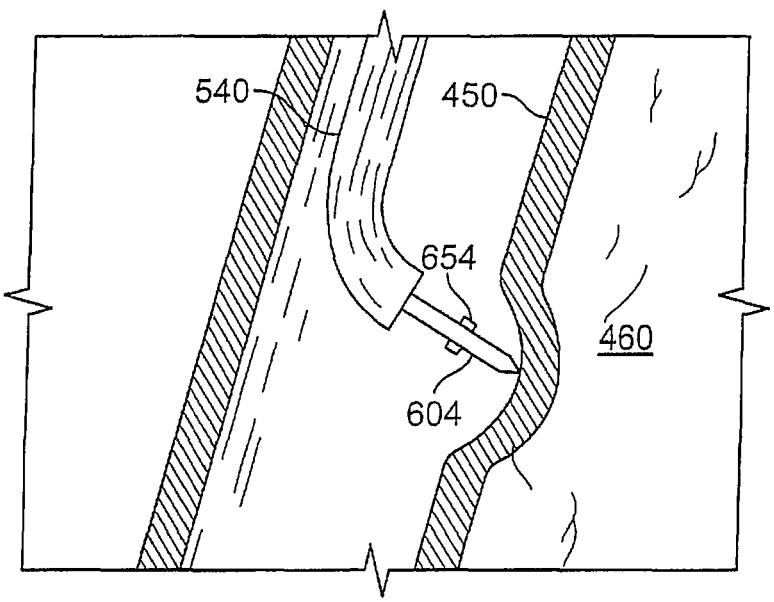

As shown in FIG. 4I, a device of insufficient sharpness will "tent" the airway wall 450. Tenting occurs when a device is placed against an airway wall with significant force but with no puncturing of the airway wall. The airway wall will deflect and become displaced until the device is withdrawn. If the tissue becomes tented there remains a significant amount of potential energy placed by the device onto the airway wall. The potential energy may unexpectedly becomes realized, when the device eventually punctures the airway, which may cause the device to suddenly plunge into the parenchyma to an unintended depth. Plunging may in turn cause unintended damage to the patient. A depth limiting feature 654 may overcome this problem.

Figure 4J:
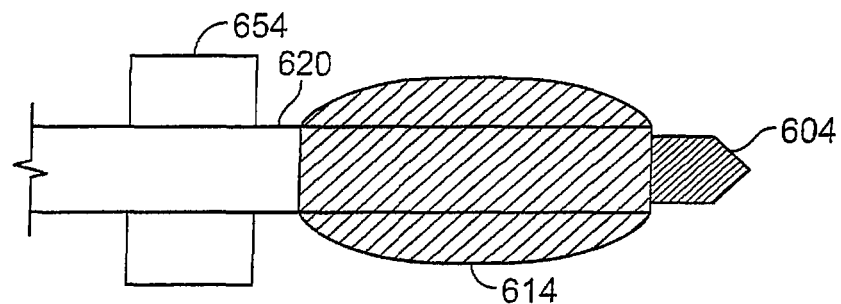

Variations of the invention include a depth limiting feature that may prevent inadvertent advancement of the device when creating the channel. One example of this may be a circular tube 654 placed over the device and set at a fixed distance (e.g. 10 mm) from the distal tip of the piercing member, proximal to the balloon, as shown in FIG. 4J. If the device does tent and plunge into the airway wall the front face of the tube may halt the plunging effect by acting as a barrier. Another example would be a secondary balloon, proximal to the channel expansion balloon, placed in a similar position to the circular tube as described above. Another example would be a folding basket formed from the outer lumen of the device, or constructed from wire.

Figure 4K:
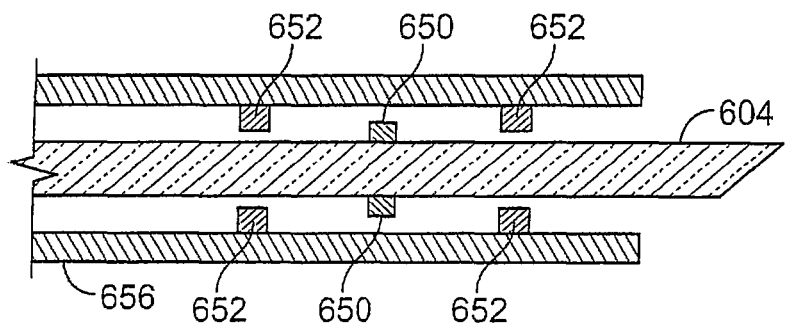

As shown in FIG. 4K, variations of the invention may include a distal collar 650 on the distal portion of the piercing member 604 to precisely limit the maximum extension and retraction of the piercing member 604. The distal collar 650 would be attached to the piercing member and travel between two set collar stops 652 which are attached to the lumen 656 the piercing member travels in. This feature has multiple benefits; first, it has the safety setting a maximum distance for the piercing member to extend, around 2-3 mm has been found to be sufficient in most cases. Thus, the maximum penetration of the piercing member 604 is limited which may prevent unintentional damage to the lung tissue.

The collar 650 protects the bronchoscope by preventing deflection of the distal tip. Deflection can take place when there is a significant amount of gap between the inner sheath 622 and the distal tip of the piercing member in the retracted mode. When the device is being maneuvered through a bronchoscope in a torturous configuration, the lumen 656 can deflect while the stiffer piercing member will not, and thus the piercing member may pierce through the deflected lumen 656 and subsequently into the bronchoscope. By setting a small gap (e.g. <1 mm) this deflection may be eliminated, and the scope protected.

The collar 650 also allows the piercing member to be reliably extended. It was found that when a similar feature was placed at the proximal section of the device the piercing member could not reliably be extended to a set distance beyond the distal tip. This is because when in a torturous configuration the outer sheath 620 of the device may have a tendency to stretch or compress. As a result the tubing may stretch to such a degree that when the piercing member is fully extended it still may not fully extend past the distal tip of the lumen 656. By locating the collar 650 in the distal portion of the lumen 656 (e.g. less than 2 inches from the distal tip) the stretching or compression is minimized or eliminated.

Conduit Deployment Devices and Methods

Figure 5A:
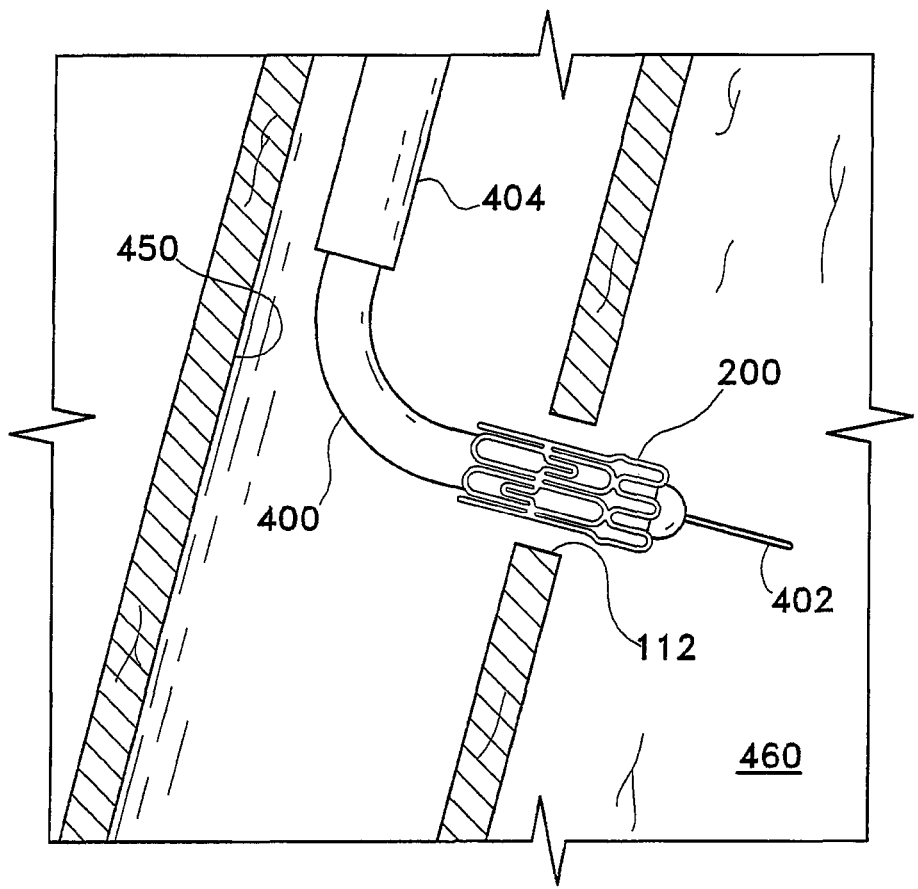
FIGS. 5A-5C illustrate a method for deploying a conduit.
Figure 5B:
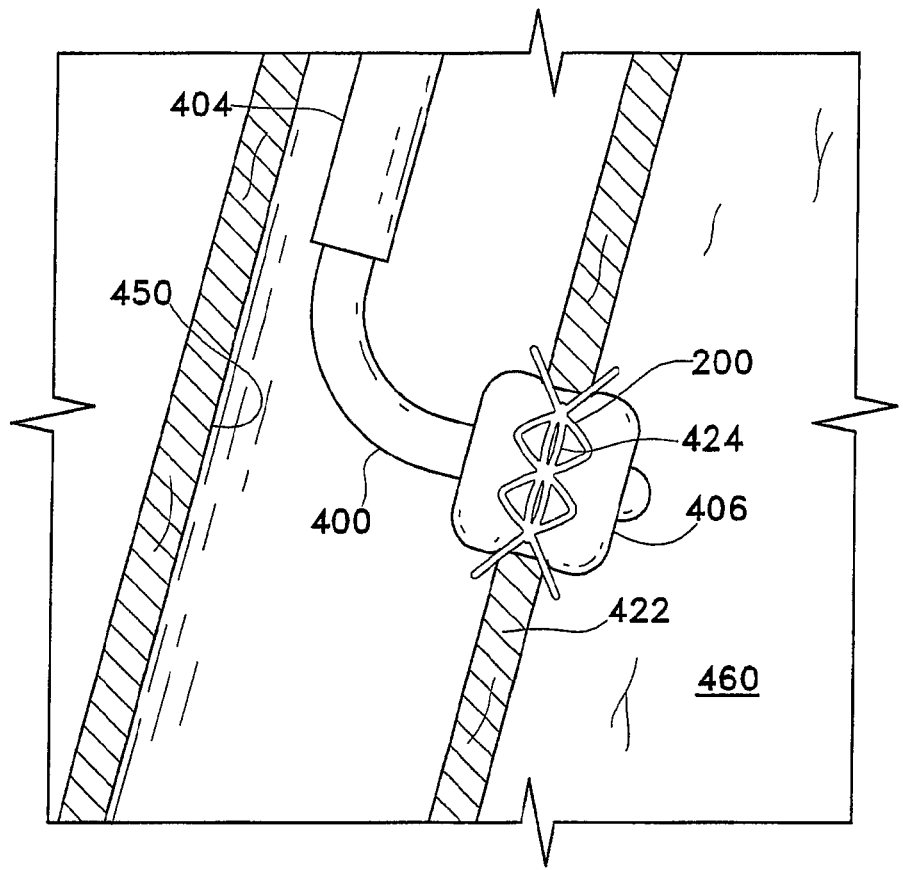
Figure 5C:
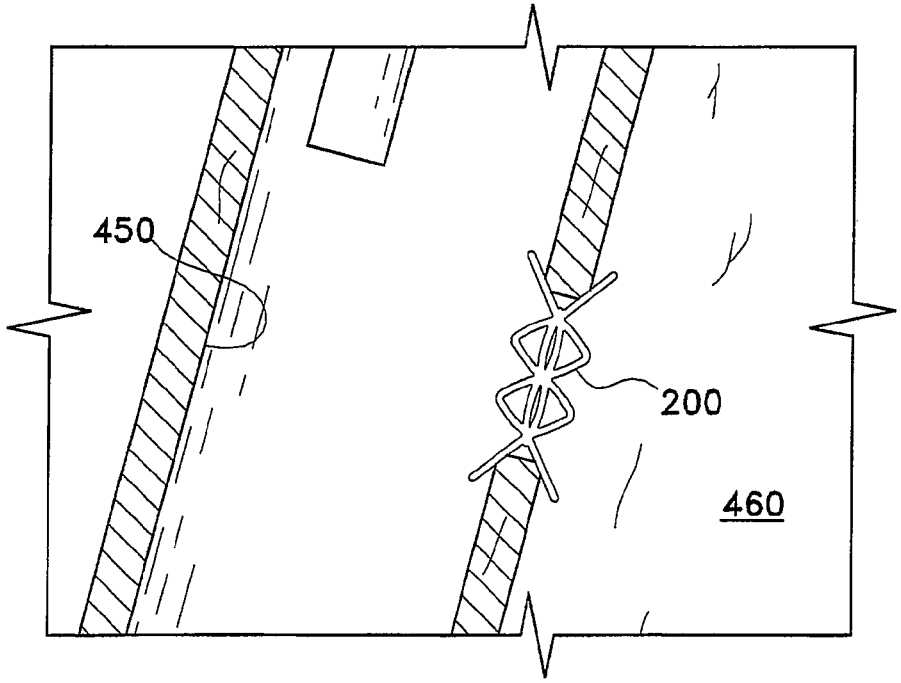

FIGS. 5A-5C illustrate a way to deploy a conduit in a channel. Referring to FIG. 5A, a delivery device 400 is loaded with a conduit 200. An access scope-type device 404 (e.g., an endoscope, a bronchoscope, or other device) may optionally be used to place the delivery device 400 into a collateral channel 112. A guide wire 402 may be used to place the delivery device 400 into the collateral channel 112. The guide wire 402 may be a conventional guide-wire or it may simply be comprised of a super-elastic material. The use of a guide wire is optional as the invention contemplates placement of the conduit 200 using only the delivery device 400.

FIG. 5A also illustrates articulation (or bending) of the deliver device 400 to access the collateral channel 112. However, the invention also contemplates articulation of the access device 404. The access device 404 may be articulated such that the delivery device 400 may advance straight into the collateral channel 112. Accordingly, the delivery device 400 may exit straight from the access device 404 or it may be articulated into the opening.

FIG. 5B illustrates deployment of the conduit 200. In particular, balloon member 406 is shown in an expanded state resulting in (1) the conduit's center section being radially expanded and (2) the conduit's extension members being outwardly deflected such that opposing extension members sandwich portions of the tissue wall 422. Diametric-control members 424 are also shown in this figure. The diametric or center-control segments limit the center section's radial expansion. In this manner, conduit 200 is securely placed in the channel to maintain a passageway through the airway wall 422.

FIG. 5C illustrates the deployed conduit 200 once the delivery device 400 is removed from the site. It should be noted that dilation of the collateral channel or opening 112 may be performed by mere insertion of the conduit 200 and/or delivery device 400.

It should be noted that deployment of conduits is not limited to that shown in FIGS. 5A-5C, instead, other means may be used to deploy the conduit. For example, spring-loaded or shape memory features may be actuated by mechanical or thermal release and unlocking methods. Additionally, mechanical wedges, lever-type devices, scissors jack devices, open chest surgical placement and other techniques may be used to deploy the conduit. Again, the conduit 200 may be comprised of an elastic or super-elastic material which is restrained in a reduced profile for deployment and expands to its deployed state upon mechanical actuator or release.

Figure 5D:
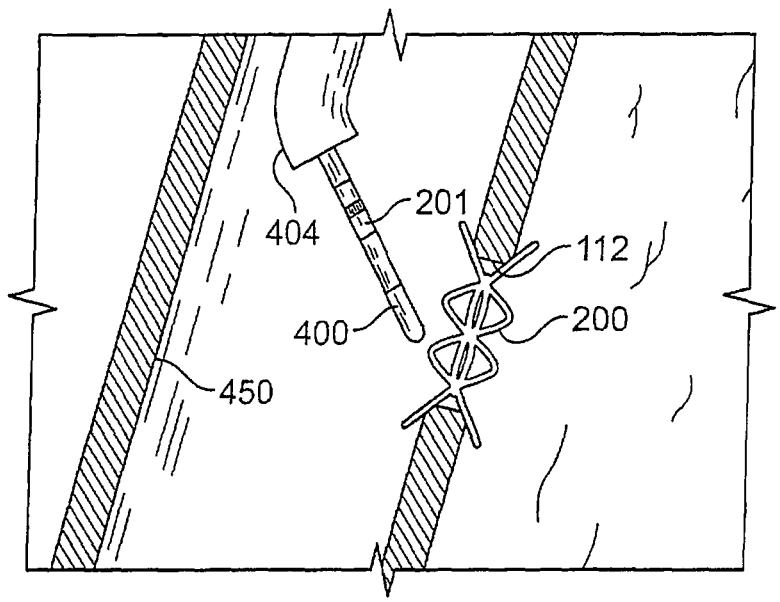
FIGS. 5D-5E illustrate a method for deploying a conduit within another implant.
Figure 5E:
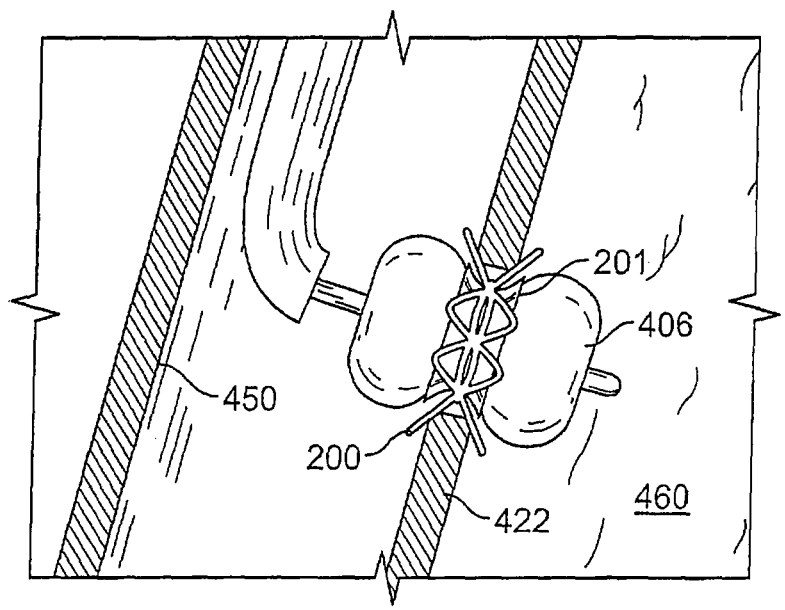

In one additional variation of the invention, as shown in FIG. 5D, a conduit 201 may be deployed within a second structure such as a second conduit or stent. Such an approach may be used to increase retention of the conduits within the channel as well as prevent closing of the channel. For example, an initial conduit 200 or stent may be deployed within the channel 112. This first conduit or stent may have certain properties that make it more acceptable to implantation within the body without generating an aggressive tissue healing response. For instance, the stent may be a drug eluting stent, or the conduit may be constructed from a bio-compatible metal without any additional tissue barrier. Once the initial stent or conduit is placed within the channel 112 a second conduit may be deployed within the first conduit. As shown in FIG. 5D, a first conduit 200 (or stent) is placed within the channel 112. FIG. 5D illustrates a second conduit 201 advanced towards the first conduit 200. FIG. 5E illustrates the second conduit 201 deployed within the first conduit 200. The second conduit 201 may have additional properties that permit the channel to remain patent. For example, the second conduit 201 my have a tissue barrier as discussed above, or other construction that generates an aggressive healing response within the lung. Therefore, the first conduit 200, being more conducive to implantation, will serve to anchor both conduits 200, 201 as the tissue either does not grow, or it grows around the outer conduit 200. The second conduit, for example, may have a tissue barrier placed thereon. Once the second conduit 201 is deployed within the first conduit 200, the tissue barrier of the second conduit 201 will prevent tissue from growing through the stent structure.

It should be noted that the structure of a conduit within a conduit may be incorporated into a single composite structure.

In use, the conduit 200 is deployed with the distal side towards the parenchymal tissue 460 while the proximal side remains adjacent or in the airway 450. Of course, where the proximal and distal extension members are identical, the conduit may be deployed with either side towards the parenchymal tissue.

Figure 6A:
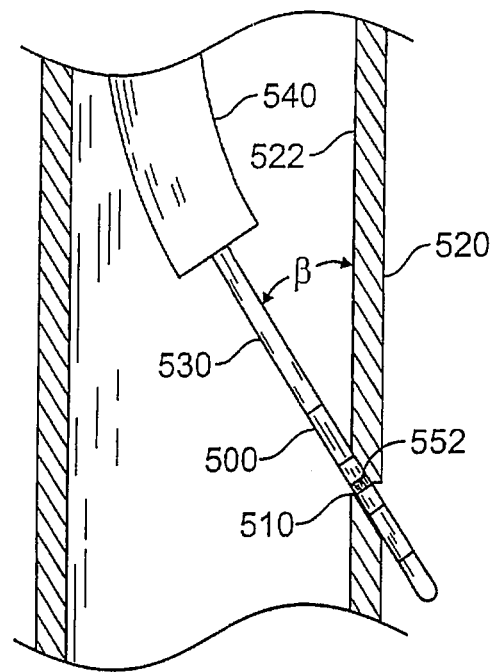
FIGS. 6A-6B illustrate a method for deploying a conduit at an angle.
Figure 6B:
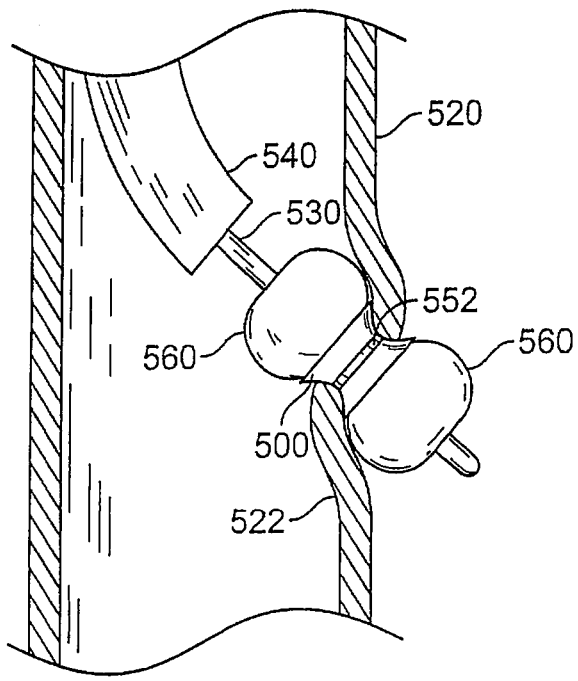

FIGS. 6A-6B illustrate another example of deploying a conduit 500 in a channel 510 (or opening) created in a tissue wall 520. Referring to FIG. 6A, a delivery tool 530 carrying a deployable conduit 500 is inserted into the channel 510. The delivery tool 530 is extended straight from an access catheter 540 such that the delivery tool forms an angle β with the tissue wall 520. It is to be understood that while the tissue wall of airway 522 is shown as being thin and well defined, the present invention may be utilized to maintain the patency of channels and openings which have less well defined boundaries. The delivery tool is further manipulated until the conduit is properly positioned which is determined by, for example, observing the position of a visualization mark 552 on the conduit relative to the opening of the channel 510.

FIG. 6B illustrates enlarging and securing the conduit in the channel using an expandable member or balloon 560. The balloon 560 may be radially expanded using fluid (gas or liquid) pressure to deploy the conduit 500. The balloon may have a cylindrical shape (or another shape such as an hourglass shape) when expanded to 1.) expand the center section and 2.) deflect the proximal and distal sections of the conduit such that the conduit is secured to the tissue wall 520. During this deployment step, the tissue wall 520 may distort or bend to some degree but when the delivery tool is removed, the elasticity of the tissue tends to return the tissue wall to its initial shape. Accordingly, the conduits disclosed herein may be deployed either perpendicular to (or non-perpendicular to) the tissue wall.

Figure 7A:
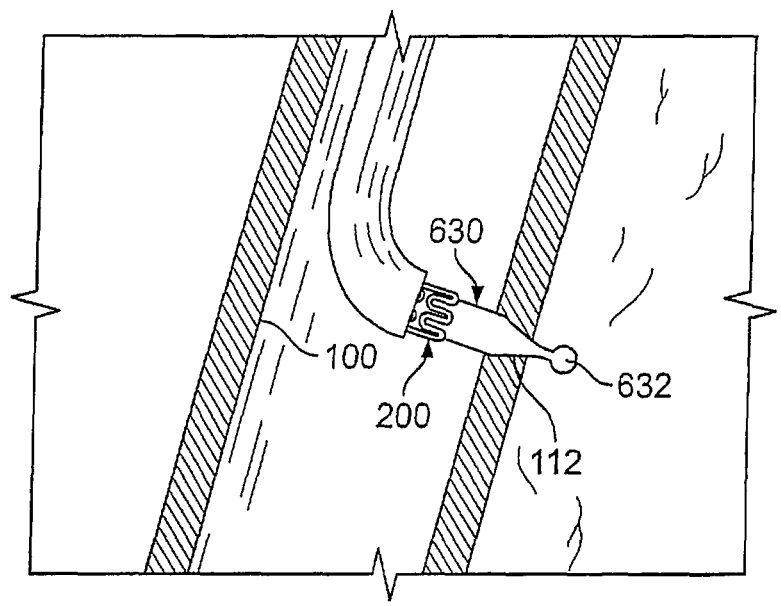
FIGS. 7A-7B illustrate placement of a conduit within a channel by using a guide member.

FIG. 7A illustrates another variation of deploying a conduit 200 into an opening 112. In some variations of the invention, prior to deployment of the conduit 200, the channel 112 may have a diameter or size that may require an additional dilation or expansion of the channel 112 for proper deployment of the conduit 200. For example, the channel 112 may be created by a piercing member, as described above, where the channel 112 nearly closes upon removal of the piercing member. However, the devices and method described herein are not limited to channels 112 of any particular size. The channels may in fact be larger than a diameter of the conduit 200 in its un-deployed state.

In any case, after creation of the channel 112 the surgeon may advance a balloon catheter 630 containing a conduit 200 towards the site of the opening 112. The variation of the balloon catheter 630 depicted in the figure also includes a guide body 632. Because the opening 112 may be difficult to locate, the guide body 632 may serve various functions to assist in locating the opening 112 and placing the conduit 200. For example, as shown in FIG. 7A, the guide body 632 may have a rounded front surface. This allows probing of the catheter 630 against the airway 100 wall to more easily locate the opening 112. The rounded surface of the guide body 632 will not drag on the airway tissue.

Figure 7B:
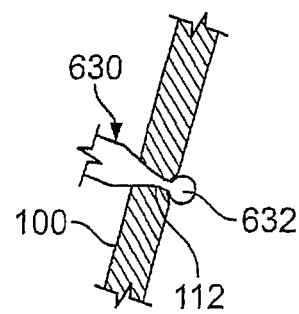

As shown in FIG. 7B, once inserted into the opening 112, the guide body 632 provides an additional function of temporarily anchoring the device 630 within the opening 112. The ability to temporarily anchor the device 630 into the opening 112 may be desirable due to the natural tidal motion of the lung during breathing. The increased surface area of the guide body 632 requires increased resistance upon remove the guide body 632 from the opening 112. Such a feature lessens the occurrence of unintended removal of the device from the site as the lung tissue moves. As shown in FIG. 7B, after insertion into the airway 100 wall, a portion of the guide body 632 serves as a resistance surface to provide the temporary anchoring function. Additional variations of the guide body 632 are shown below.

FIGS. 8A-8F illustrate additional variations of guide bodies 632 for use with the present invention. As shown, the guide body 632 is located on the distal end of the balloon catheter 630. The guide body 632 will have a front surface 634 that is preferably smooth such that it can easily be moved over the airway wall. Proximal to the front surface 634, the guide body 632 will have at least one resistance surface 636 which is defined as an area that causes increased resistance upon removal of the guide body 634 from the airway wall. As shown, the resistance surface 636 will be adjacent to an area of reduced diameter 638 to which allows the guide body 632 to nest within the opening 112 in the airway wall. The guide body 632 may have any number of shapes as shown in the figures.

Figure 8A:
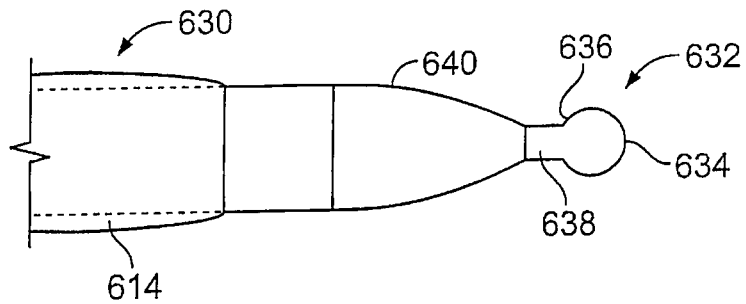
FIGS. 8A-8F illustrate additional variations of guide bodies for use with catheters of the present invention.
Figure 8B:
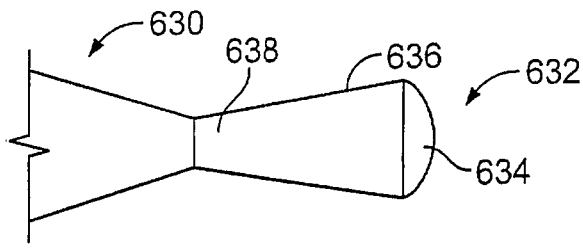
Figure 8C:
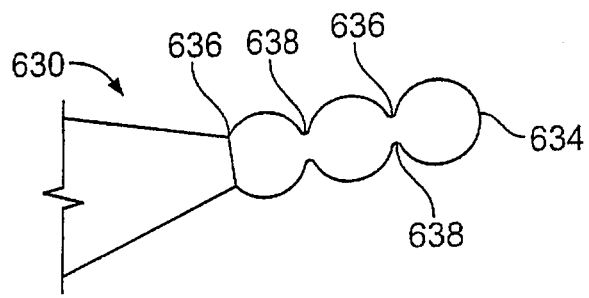
Figure 8D:
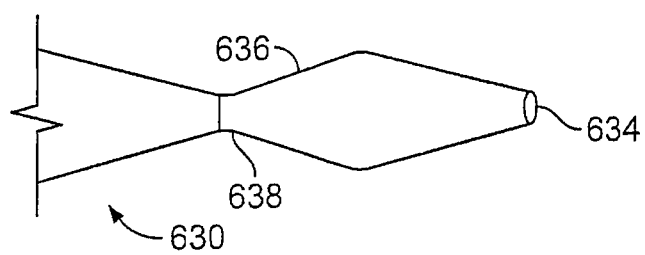
Figure 8E:
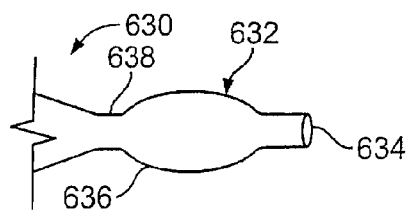
Figure 8F:
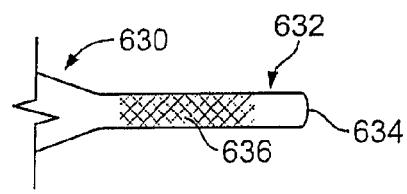

FIG. 8F illustrates another variation of a guide body 632 having a resistance surface 636 which comprises an area of increased surface roughness such that the surface will drag upon the airway wall or tissue surrounding the channel 112. Such a feature may be combined with the variations of the guide members provided above.

The balloon catheters 630 of the present invention may include a dilating member between the guide body 632 and balloon 614. In the variation shown in FIG. 8A, the dilating member comprises a tapered section 640. However, the invention is not limited as such. For example, the dilating member may comprise a second inflatable balloon, or other expanding device. The dilating members may also be retractable within the elongate shaft.

Figure 9A:
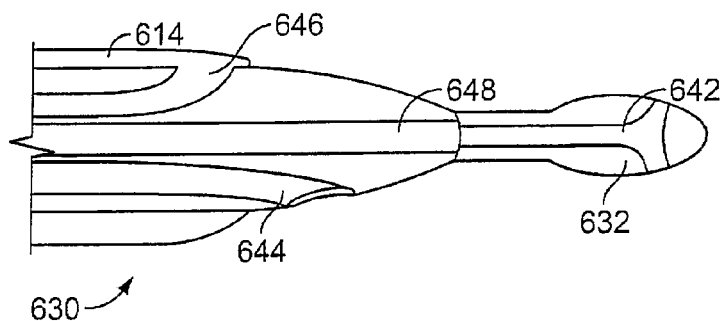
FIGS. 9A-9B illustrate additional features for use with guide bodies of the present invention.
Figure 9B:
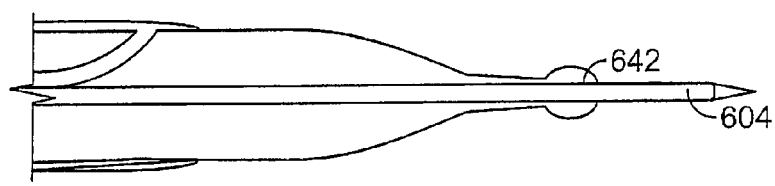

FIGS. 9A and 9B depict cross sections of examples of a balloon catheter 630 having a guide body 632 that includes a lumen 642 which terminates at a surface of the guide body 632. The lumen 642 may be used for suction, irrigation, or deliver bio-active substances, etc. The catheter 630 may also have an additional lumens 646, 646, 648 as shown, for inflation of the balloon 614 and for additional suction 644, and for communication with the guide body lumen 642. As shown in FIG. 8B, the lumen may also be used to advance a piercing member 604 to the airway wall to create the channel 112.

Any of the balloons described herein may be distensible balloons (e.g., they assume a predetermined shape upon expansion) or elastic balloons (e.g., simply expand). Use of a distensible balloon permits control in dilating the opening 112 or placement of the conduit.

Delivery of Medications/Substances to Parenchymal Tissue

In an additional variation, a medical practitioner may create a channel to delivery substances such as bioactive agents, medications, therapeutic substances, or other such materials through the airway wall and directly to the parenchymal tissue of the lung.

In such a case, the practitioner engages many of the steps outlined above such as identifying regions of having severe occurrences of trapped gas or tissue destruction. However, the methods and channel creation techniques described herein may also be suitable for a variety of other disease states affiliated with the lung (especially cancer and treatment of tumors or other growths). In the latter cases, an x-ray, ultrasound, Doppler, acoustic, MRI, PET, computed tomography (CT) scans and/or other non-invasive imaging technique may be employed to locate the region of diseased tissue (such as a tumor). In some cases, if the channel is created solely for the purpose of delivering a substance, then the channel patency techniques described herein may no longer be applicable. Instead, after delivery of the substance, the medical practitioner may desire closure of the channel.

Once the practitioner identifies a region for creation of the channel, the practitioner may then search for a safe location to penetrate the airway wall (such as using the blood vessel detection techniques described above.

Figure 10A:
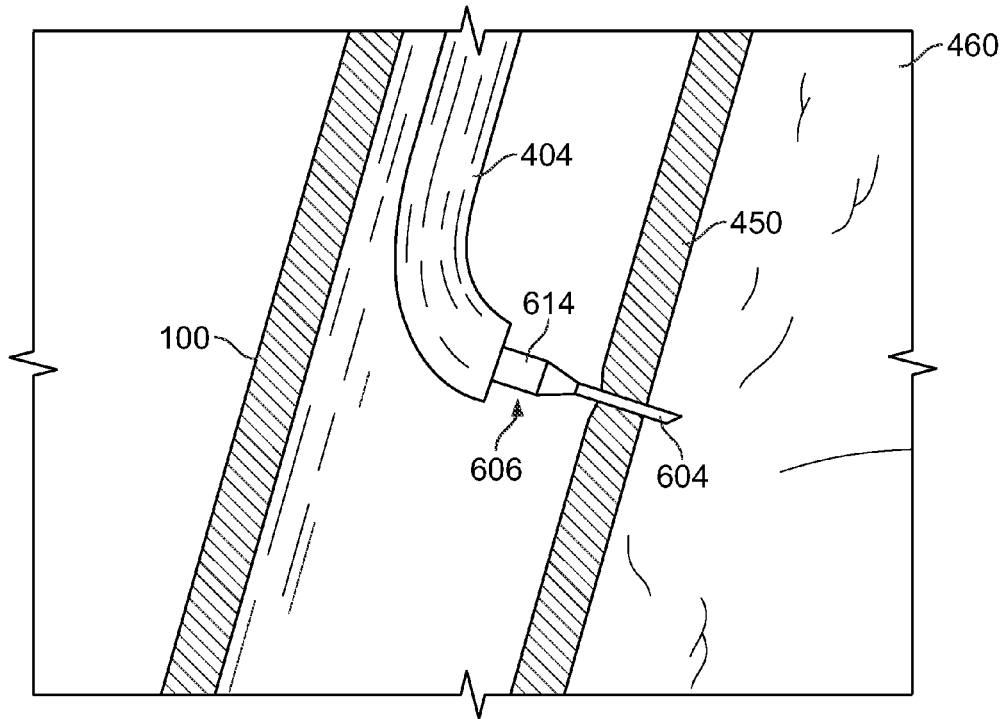
FIGS. 10A-10B respectively illustrate delivery of substances through an opening in the airway and through a conduit placed within the opening.

After finding a suitable location, the practitioner creates the opening or channel. Again, any technique described herein may be used to create the channel. However, FIG. 10A illustrates an example in which a substance may be delivered during creation of the channel. In this example, a similar balloon catheter 606 as described above may have a piercing member 604 that penetrates the airway wall 450. Once through, the practitioner may inject the desired substance into parenchymal tissue 460. Although the illustration shows the piercing member 604 as extending slightly past the airway wall 450, variations of the method include delivering a substance to any location beyond the wall.

Figure 10B:
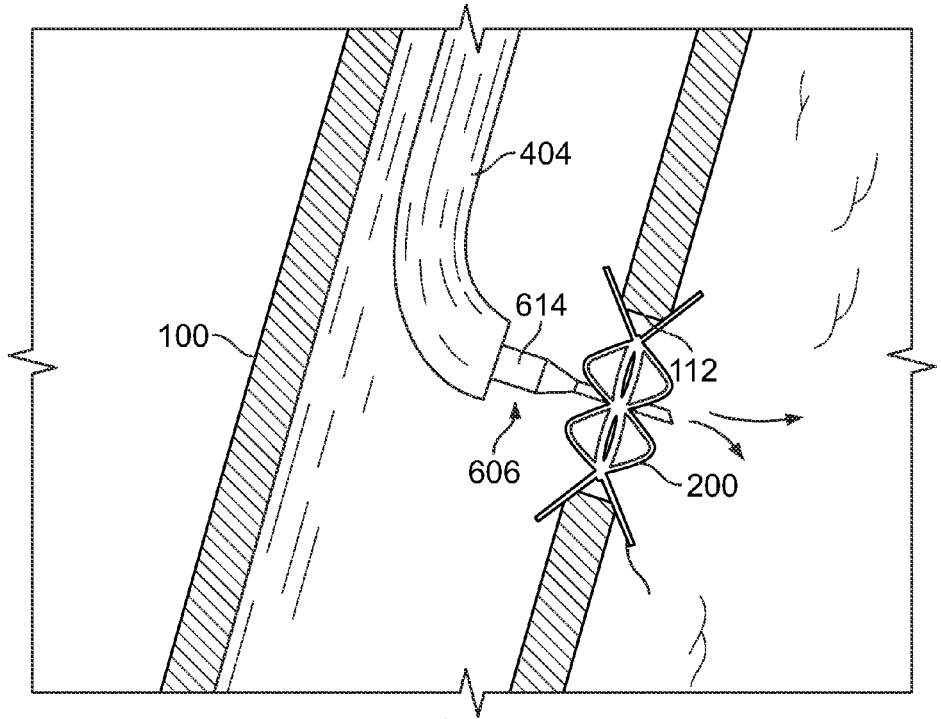

FIG. 10B illustrates another variation of the method. As shown, a substance may be delivered through an existing channel/opening 112. As shown, a catheter 606 can inject the substance through the channel/opening 112 to the tissue. The method may include delivering the substance through a opening 112 with or without an implant 200. In this variation, the channel 112 also includes an implant 200 within the opening 112 with the substance being delivered through the implant 200. Use of an implant 200 may be desirable in those cases where trapped gasses must be evacuate as well as those cases where repeat treatment of a site is planned (e.g., tumor treatment). In addition, the implant 200 may be removed from the channel 112 to either promote or inhibit healing depending on the desired benefit. Naturally, this treatment may be performed in more than one location in the lung, depending on the areas of intended treatment and/or diseased tissue. As noted above, the existing channel/opening 112 can be created such that patency of the existing surgically created opening is extended beyond at least creation of the surgically created opening.

The substances that may be delivered as described above may include any of the substances described herein. In addition, examples of bioactive substances include, but are not limited to, antimetabolites, antithrobotics, anticoagulants, antiplatelet agents, thorombolytics, antiproliferatives, antinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium, epithelium) and tissue formation (neointimal tissue).

Still other bioactive agents include but are not limited to analgesics, anticonvulsives, anti-infectives (e.g., antibiotics, antimicrobials), antineoplastics, H2 antagonists (Histamine 2 antagonists), steroids, non-steroidal anti-inflammatories, hormones, immunomodulators, mast cell stabilizers, nucleoside analogues, respiratory agents, antihypertensives, antihistamines, ACE inhibitors, cell growth factors, nerve growth factors, anti-angiogenic agents or angiogenesis inhibitors (e.g., endostatins or angiostatins), tissue irritants (e.g., a compound comprising talc), poisons (e.g., arsenic), cytotoxic agents (e.g., a compound that can cause cell death), various metals (silver, aluminum, zinc, platinum, arsenic, etc.), epithelial growth factors or a combination of any of the agents disclosed herein.

Examples of agents include pyrolitic carbon, titanium-nitride-oxide, taxanes, fibrinogen, collagen, thrombin, phosphorylcholine, heparin, rapamycin, radioactive 188Re and 32P, silver nitrate, dactinomycin, sirolimus, everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, 7-epi-taxol, cephalomannine, baccatin III, baccatin V, 10-deacetylbaccatin III, 7-epi-10-deacetylbaccatin III, docetaxel.

In addition, the substances may be selected to induce a biologic lung volume reduction such as by using a talc compound, lung irritant, or fibrin hyrogels containing fibroblast growth factor-1. The use of such compounds may be found in: U.S. patent application Ser. No. 09/590,790, filed Jun. 8, 2000 entitled MINIMALLY INVASIVE LUNG VOLUME REDUCTION ASSEMBLY AND METHOD; U.S. patent application Ser. No. 10/679,065 filed Oct. 3, 2003 entitled MINIMALLY INVASIVE LUNG VOLUME REDUCTION ASSEMBLY AND METHOD; and FIBROBLASTS GROWTH FACTOR-1 THERAPY FOR ADVANCED EMPHYSEMA—A NEW TISSUE ENGINEERING APPROACH FOR ACHIVEING LUNG VOLUME REDUCTION to Ingenito et al. J. Bronchol, Vol. 1, Jul. 3, 2006.

All publications, patent applications, patents, and other references mentioned herein are incorporated by reference in their entirety. To the extent there is a conflict in a meaning of a term, or otherwise, the present application will control. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is also contemplated that combinations of the above described embodiments/variations or combinations of the specific aspects of the above described embodiments/variations are within the scope of this disclosure.

EXAMPLE

Implant

Implants comprising stainless steel mesh frame fully encapsulated with a composition comprising silicone (as described below) and paclitaxel were implanted in several canine models. Visual observation indicated that, on average, the passage through the implants of the present invention remained unobstructed and were associated with significantly reduced fibrotic and inflammatory responses, in canine models, at a considerably higher rate than an implant without any drug adjunct or coronary drug eluting stents (as shown in FIG. 12).

The composition comprised approximately a 9% paclitaxel to silicone ratio with approximately 400 micrograms of paclitaxel per implant. Measurements found that approximately 30% of the paclitaxel released after 60 days. In general, for implants with the paclitaxel/silicone composition, observations of chronic inflammation, epithelial metaplasia and fibrosis were all very mild.

For paclitaxel as the bioactive substance, polymers with solubility parameters between 5-25 $(MPa)^{1/2}$ were believed to provide sufficient elution rates. The polymer used in the example device has good diffusivity for lipophilic drug (such as paclitaxel) because the side methyl group on the silicone may be substituted with more lipophilic hydrocarbon molecules containing vinyl group or groups in addition polymerization by platinum catalyst.

The composition for the example may be as follow: polymer part: polydimethylsiloxane, vinyldimethyl terminated, any viscosity; and/or polydimethylsiloxane, vinylmonomethyl terminated, any viscosity. The cross-linker part: polydimethylsiloxane, any viscosity; and or polymonomethylsiloxane, any viscosity. Platinum catalyst part and/or cross-linker part: platinum; and/or platinum-divinyltetramethyldisiloxane complex in xylene, 2-3% Pt; and/or platinum-divinyltetramethyldisiloxane complex in vinyl terminated polydimethylsiloxane, 2-3% Pt; and/or platinum-divinyltetramethyldisiloxane complex in vinyl terminated polydimethylsiloxane, ~1% Pt; platinum-Cyclovinylmethylsiloxane complex, 2-3% Pt in cyclic vinyl methyl siloxane.

These components may be combined in different ratios to make the polymer. The hydrocarbon side chain off the silicone back bone makes this polymer system unique and may result in a "zero-order"-like release profile. The amount of vinyl siloxane cross-linker may determine the rate of the drug release and diffusivity of the polymer to the drug. There are other types of polydimethylsiloxanes such as: trimethylsiloxy terminated polydimethylsiloxane in various viscosities, (48-96%) dimethyl (4-52%) diphenylsiloxane copolymer in various viscosities, dimethylsiloxane-ethylene oxide copolymer, dimethyl diphenylsiloxane copolymer, polymethylhydrosiloxane, trimethylsilyl terminated at various viscosities, (30-55%) methyldro-(45-70%) dimethylsiloxane copolymer at various viscosities, polymethylphenylsiloxane, polydimethylsiloxane silanol terminated at various viscosities, polydimethylsiloxane aminopropyldimethyl terminated at various viscosities. For paclitaxel a release profile was found to be acceptable with a polymer system consisting of polydimethylsiloxane vinyl terminated at various viscosity and a range of platinum-mono, di, tri and/or tetramethyldisiloxane complex.

We claim:

1. A method of accessing lung tissue through an opening in an airway wall, the method comprising:
   advancing a catheter into the lung;
   advancing the catheter through the opening in the airway wall to access a treatment site in lung tissue beyond the airway wall;
   accessing the treatment site using the catheter; and
   performing a procedure at the treatment site.

2. The method of claim 1, wherein accessing the treatment site using the catheter and performing a procedure at the treatment site comprises delivering a substance through the opening to treat a region of diseased tissue beyond the airway wall in the lung.

3. The method of claim 2, wherein the step of delivering the substance through the opening comprises delivering the substance through the opening to treat a tumor.

4. The method of claim 2, wherein the substance comprises a substance selected from the group consisting of antimetabolites, antithrobotics, anticoagulants, antiplatelet agents, thorombolytics, antiproliferatives, anti-inflammatories, agents that inhibit hyperplasia, agents that inhibit restenosis, anti-angiogenic agents or angiogenesis inhibitors, smooth muscle cell inhibitors, growth factors, growth factor inhibitors, cell adhesion inhibitors, cell adhesion promoters and a combination thereof.

5. The method of claim 1, further comprising preventing closure of the opening wherein said preventing step is performed using a mechanical means.

6. The method of claim 5, wherein said mechanical means comprises an act selected from the group consisting of a) inserting an implant within and b) dilating the opening.

7. The method of claim 1, further comprising creating the opening.

8. The method of claim 1 wherein the catheter comprises a rounded distal end.

9. A method of accessing lung tissue through an opening in an airway wall, the method comprising:
  advancing a catheter into the lung;
  advancing a rounded end of the catheter through the opening in the airway wall to access a treatment site in lung tissue beyond the airway wall;
  accessing the treatment site using the catheter; and
  performing a procedure at the treatment site.

10. The method of claim 9, wherein performing a procedure at the treatment site using the catheter comprises delivering a substance through the opening to treat a region of diseased tissue beyond the airway wall in the lung.

11. The method of claim 10, wherein the step of delivering the substance through the opening comprises delivering the substance through the opening to treat a tumor.

12. The method of claim 10, further comprising creating the opening.

13. The method of claim 9, further comprising preventing closure of the opening wherein said preventing step is performed using a mechanical means.

14. The method of claim 13, wherein said mechanical means comprises an act selected from the group consisting of a) inserting an implant within and b) dilating the opening.

15. A method of accessing lung tissue through an opening in an airway wall, the method comprising:
  advancing a catheter into the lung;
  enlarging the opening;
  advancing a rounded end of the catheter into the opening in the airway wall to access a treatment site in lung tissue beyond the airway wall;
  preventing closure of the opening;
  accessing the treatment site using the catheter; and
  performing a procedure at the treatment site.

16. The method of claim 15, wherein performing a procedure at the treatment site using the catheter comprises delivering a substance through the opening to treat a region of diseased tissue beyond the airway wall in the lung.

17. The method of claim 15, further comprising delivering electrical energy with the catheter.

18. The method of claim 15, wherein preventing closure of the opening is performed using a mechanical means.

19. The method of claim 18, wherein said mechanical means comprises an act selected from the group consisting of a) inserting an implant in the opening, b) dilating the opening, and c) temporarily holding open the opening with an instrument.

20. The method of claim 15, wherein a piercing member is withdrawn from the opening prior to advancing the rounded end of the catheter.

* * * * *